US007576235B2

(12) United States Patent
Carlini et al.

(10) Patent No.: US 7,576,235 B2
(45) Date of Patent: Aug. 18, 2009

(54) PROCESSES FOR PREPARING BIS(UREA-URETHANE) COMPOUNDS

(75) Inventors: Rina Carlini, Mississauga (CA); Adela Goredema, Mississauga (CA); Eniko Toma, Mississauga (CA); Christine E. Bedford, Burlington (CA)

(73) Assignee: Xerox Corporation, Norwalk, CT (US)

( * ) Notice: Subject to any disclaimer, the term of this patent is extended or adjusted under 35 U.S.C. 154(b) by 497 days.

(21) Appl. No.: 11/097,758

(22) Filed: Apr. 1, 2005

(65) Prior Publication Data

US 2006/0122415 A1 Jun. 8, 2006

Related U.S. Application Data

(60) Provisional application No. 60/633,331, filed on Dec. 4, 2004.

(51) Int. Cl.
C07C 261/00 (2006.01)
C07C 269/00 (2006.01)
(52) U.S. Cl. .......................... 560/25; 560/158
(58) Field of Classification Search .................. 560/25, 560/158
See application file for complete search history.

(56) References Cited

U.S. PATENT DOCUMENTS

| 4,314,924 | A | * | 2/1982 | Haubennestel et al. ...... 524/779 |
|---|---|---|---|---|
| 4,384,102 | A | | 5/1983 | Rasshofer et al. ............. 528/73 |
| 4,566,981 | A | | 1/1986 | Howells ..................... 252/8.8 |
| 6,420,466 | B1 | * | 7/2002 | Haubennestel et al. ...... 524/195 |
| 6,548,476 | B1 | | 4/2003 | Wu et al. ....................... 514/2 |
| 2001/0044553 | A1 | | 11/2001 | Kabashima et al. ......... 560/157 |
| 2003/0079644 | A1 | | 5/2003 | Smith et al. ............... 106/31.29 |
| 2003/0105185 | A1 | | 6/2003 | Goodbrand et al. ......... 523/160 |
| 2004/0060474 | A1 | | 4/2004 | Boils-Boissier et al. .. 106/31.29 |
| 2004/0065227 | A1 | | 4/2004 | Breton et al. ............. 106/31.29 |
| 2004/0075723 | A1 | | 4/2004 | Breton et al. ................. 347/99 |
| 2004/0158063 | A1 | | 8/2004 | Boils-Boissier et al. ..... 544/180 |

FOREIGN PATENT DOCUMENTS

| EP | 0 056 153 | | 12/1985 |
|---|---|---|---|
| EP | 0 160 402 | B1 | 7/1991 |
| EP | 1 067 157 | A1 | 1/2001 |
| EP | 1 350 507 | A1 | 10/2003 |
| EP | 1 422 073 | A1 | 5/2004 |
| WO | WO 00/55149 | | 9/2000 |
| WO | WO 03/040135 | | 5/2003 |
| WO | WO 03/084508 | | 10/2003 |
| WO | WO 2005/047231 | A | 5/2005 |

OTHER PUBLICATIONS

Van Esch J et al., "Di-urea Compounds as Gelators for Organic Solvents", Tetrahedron Letters, Elsevier, Amsterdam, NL, vol. 38, No. 2, Jan. 13, 1997, pp. 281-284.

Versteegen, Ron M et al., "Synthesis and Characterization of Segmented Copoly(ether urea)s With Uniform Hard Segments", Macromolecules, 38(8), 3176-3184 CODEN: Mamobx: ISSN: 0024-9297, Mar. 24, 2005, p. 3180.

Carr A J et al., "The Design of Organic Gelators: Solution and Solid State Properties of a Family of Bis-Ureas", Tetrahedron Letters, Elsevier, Amsterdam N, vol. 39, No. 41, ISSN: 0040-4039, Oct. 8, 1988, pp. 7447-7450.

Copending U.S. Appl. No. 11/004,682, filed Dec. 4, 2004, entitled "Trans-1,2-cyclohexane bis[urea-urethane] Compounds," with the named inventors Adela Goredema, Rina Carlini, Marcel P. Breton, Jeffery H. Banning, and Eniko Toma.

(Continued)

Primary Examiner—Taylor Victor Oh
(74) Attorney, Agent, or Firm—Oliff & Berridge, PLC

(57) ABSTRACT

Processes for preparing bis(urea-urethane) compounds

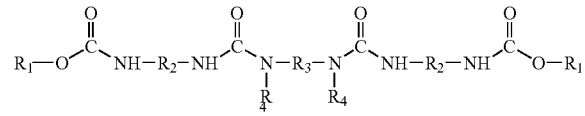

wherein $R_1$ is alkyl, aryl, arylalkyl, or alkylaryl, $R_2$ is alkylene, arylene, arylalkylene, or alkylarylene, $R_3$ is alkylene, arylene, arylalkylene, or alkylarylene, and $R_4$ is hydrogen or alkyl, comprising: (1) first bring to a reaction temperature of about 20-125° C. a reaction mixture comprising monoalcohol reactant $R_1$—OH and diisocyanate reactant OCN—$R_2$—NCO, the monoalcohol being present in an amount of about 0.8-1.2 moles monoalcohol per mole diisocyanate, the monoalcohol and diisocyanate reactants being admixed in a solvent, the reactants and solvent being present in relative amounts of at least about 1 milliliter solvent per millimole diisocyanate, the reaction temperature continuing until reaction between the monoalcohol and the diisocyanate is complete; and (2) subsequent to step (1), adding to the reaction mixture diamine

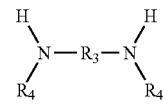

without isolating the reaction product of step (1), thereby forming compound of the formula

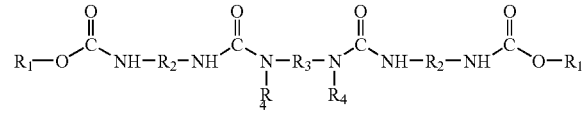

in desirably high yield and purity.

20 Claims, No Drawings

OTHER PUBLICATIONS

Copending U.S. Appl. No. 11/004,332, filed Dec. 4, 2004, entitled "Phase Change Inks Containing *Trans*-1,2-cyclohexane bis[urea-urethane] Compounds," by Adela Goredema et al.

Copending U.S. Appl. No. 11/004,331, filed Dec. 4, 2004, entitled "Bis[urea-urethane] Compounds and Phase Change Inks Containing Same," by Adela Goredema et al.

Copending U.S. Appl. No. 11/004,333, filed Dec. 4, 2004, entitled "Phase Change Inks Containing Bis[urea-urethane] Compounds," by Adela Goredema et al.

Copending U.S. Appl. No. 11/004,761, filed Dec. 4, 2004, entitled "Curable *Trans*-1,2-cyclohexane bis[urea-urethane] Compounds," by Rina Carlini et al.

Copending U.S. Appl. No. 11/004,451, filed Dec. 4, 2004, entitled "Phase Change Inks Containing Curable *Trans*-1,2-cyclohexane bis[urea-urethane] Compounds," by Rina Carlini, et al.

"Cyclic Bis-Urea Compounds as Gelators for Organic Solvents," J. van Esch et al., *Chem. Eur. J.* 1999, 5, No. 3, pp. 937-950.

"The Design of Organic Gelators Based on a Family of Bis-Ureas," R. E. Meléndez et al., *Mat. Res. Soc. Symp. Proc.* 2000, 604, pp. 335-340.

"Formation of Organogels by Intermolecular Hydrogen Bonding Between Ureylene Segment," K. Hanabusa et al., *Chem. Lett.* 1996 pp. 885-886.

"Low Molecular Weight Gelators for Organic Solvents," J. van Esch et al., in *Supramolecular Science: Where Is It and Where It Is Going*, R. Ungaro and E. Dalcanale, Eds., 1999, Netherlands: Kluwer Academic Publishers, pp. 233-259.

"Organogels and Low Molecular Mass Organic Gelators," D. J. Abdallah and R. G. Weiss, *Adv. Mater.* 2000, 12, No. 17, Sep. 1, pp. 1237-1247.

"Remarkable Stabilization of Self-Assembled Organogels by Polymerization," M. de Loos et al., *J. Am. Chem. Soc.* 1997, 119, 12675-12676.

"Low-molecular weight organogelators," P. Terech, in *Specialist Surfactants*, I.D. Robb, Ed., 1997, London: Chapman & Hall, pp. 208-268.

"New Functional Materials Based on Self-Assembling Organogels: From Serendipity Towards Design," J. H. van Esch and B. L. Feringa, *Angew. Chem. Int. Ed.* 2000, 39, No. 13, pp. 2263-2266.

"Synthesis and Self-Assembling Properties of Polymerizable Organogelators," G. Wang and A. D. Hamilton, *Chem. Eur. J.* 2002, 8, No. 8, pp. 1954-1961.

"Low Molecular Mass Gelators of Organic Liquids and the Properties of their Gels," P. Terech and R.G. Weiss, *Chem. Rev.* 1997, 97; pp. 3133-3159.

"Towards a Phenomenological Definition of the Term 'Gel'," K. Amdal et al., *Polymer Gels and Networks*, 1993, 1, pp. 5-17.

English abstract for PCT Patent Publication WO 00/55149.
English abstract for EP 1 048 681.
English abstract for JP 10310633.
English abstract for JP 59030919.

* cited by examiner

PROCESSES FOR PREPARING BIS(UREA-URETHANE) COMPOUNDS

This application is based on a provisional patent application No. 60/633,331, filed Dec. 4, 2004, the disclosure of which is totally incorporated herein by reference.

CROSS-REFERENCE TO RELATED APPLICATIONS

Copending application U.S. Ser. No. 11/004,682, filed Dec. 4, 2004, entitled "Trans-1,2-cyclohexane bis(urea-urethane) Compounds," with the named inventors Adela Goredema, Rina Carlini, Marcel P. Breton, Jeffery H. Banning, and Eniko Toma, the disclosure of which is totally incorporated herein by reference, discloses trans-1,2-cyclohexane bis(urea-urethane) compounds of the formulae

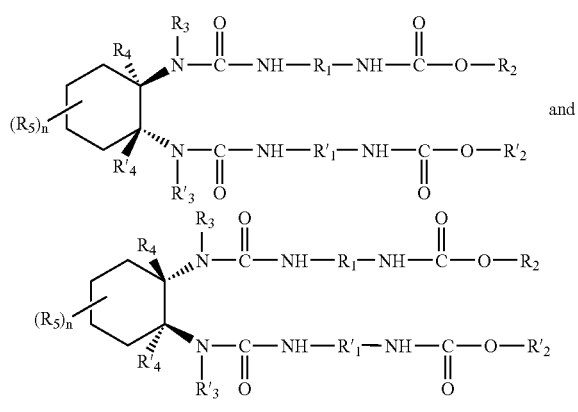

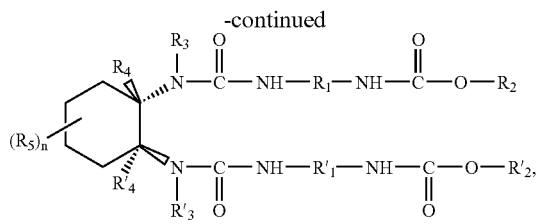

wherein $R_1$ and $R'_1$ each, independently of the other, is an alkylene group, an arylene group, an arylalkylene group, or an alkylarylene group, $R_2$ and $R'_2$ each, independently of the other, is an alkyl group, an aryl group, an arylalkyl group, or an alkylaryl group, $R_3$ and $R'_3$ each, independently of the other, is a hydrogen atom or an alkyl group, $R_4$ and $R'_4$ each, independently of the other, is a hydrogen atom, a fluorine atom, an alkyl group, or a phenyl group, n is an integer of 0, 1, 2, 3, or 4, and $R_5$ is an alkyl group, an aryl group, an arylalkyl group, an alkylaryl group, or a substituent other than an alkyl, aryl, arylalkyl, or alkylaryl group.

Copending application U.S. Ser. No. 11/004,332, filed Dec. 4, 2004, entitled "Phase Change Inks Containing Trans-1,2-cyclohexane bis(urea-urethane) Compounds," with the named inventors Adela Goredema, Rina Carlini, Marcel P. Breton, and Jeffery H. Banning, the disclosure of which is totally incorporated herein by reference, discloses phase change inks comprising a phase change ink carrier and a trans-1,2-cyclohexane bis(urea-urethane) compound of the formula

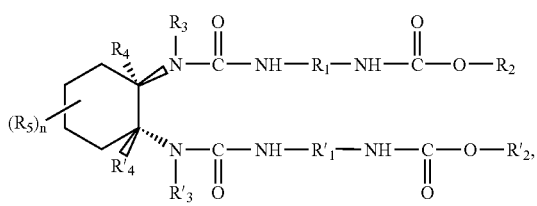

or mixtures thereof, wherein $R_1$ and $R'_1$ each, independently of the other, is an alkylene group, an arylene group, an arylalkylene group, or an alkylarylene group, $R_2$ and $R'_2$ each, independently of the other, is an alkyl group, an aryl group, an arylalkyl group, or an alkylaryl group, $R_3$ and $R'_3$ each, independently of the other, is a hydrogen atom or an alkyl group, $R_4$ and $R'_4$ each, independently of the other, is a hydrogen atom, a fluorine atom, an alkyl group, or a phenyl group, n is an integer of 0, 1, 2, 3, or 4, and $R_5$ is an alkyl group, an aryl group, an arylalkyl group, an alkylaryl group, or a substituent other than an alkyl, aryl, arylalkyl, or alkylaryl group.

Copending application U.S. Ser. No. 11/004,331, filed Dec. 4, 2004, entitled "Bis(urea-urethane) Compounds and Phase Change Inks Containing Same," with the named inventors Adela Goredema, Rina Carlini, Christine E. Bedford, Marcel P. Breton, and Eniko Toma, the disclosure of which is totally incorporated herein by reference, discloses a bis(urea-urethane) compound of the formula

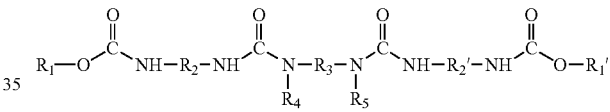

wherein $R_1$ and $R_1'$ each, independently of the other, is an alkyl group, wherein at least one of $R_1$ and $R_1'$ has at least about 6 carbon atoms, $R_2$ and $R_2'$ each, independently of the other, is an alkylene group, wherein at least one of $R_2$ and $R_2'$ has at least about 3 carbon atoms, $R_3$ is an alkylene group having at least about 2 carbon atoms, and $R_4$ and $R_5$ each, independently of the other, is a hydrogen atom or an alkyl group, and wherein $R_1$ and $R_1'$ each contain no more than 2 fully fluorinated carbon atoms.

Copending application U.S. Ser. No. 11/004,333, filed Dec. 4, 2004, entitled "Phase Change Inks Containing Bis (urea-urethane) Compounds," with the named inventors Adela Goredema, Rina Carlini, Christine E. Bedford, and Marcel P. Breton, the disclosure of which is totally incorporated herein by reference, discloses a phase change ink composition comprising a phase change ink carrier and a bis(urea-urethane) compound of the formula

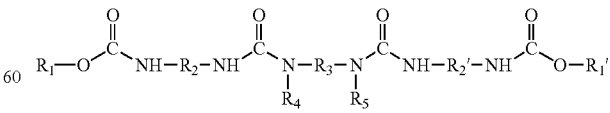

wherein $R_1$ and $R_1'$ each, independently of the other, is an alkyl group, an aryl group, an arylalkyl group, or an alkylaryl group, $R_2$ and $R_2'$ each, independently of the other, is an alkylene group, an arylene group, an arylalkylene group, or an alkylarylene group, $R_3$ is an alkylene group, an arylene group, an arylalkylene group, or an alkylarylene group, and $R_4$ and $R_5$ each, independently of the other, is a hydrogen atom or an alkyl group.

Copending application U.S. Ser. No. 11/004,761, filed Dec. 4, 2004, entitled "Curable Trans-1,2-cyclohexane bis(urea-urethane) Compounds," with the named inventors Rina Carlini, Eniko Toma, Peter G. Odell, and Jeffery H. Banning, the disclosure of which is totally incorporated herein by reference, discloses Curable trans-1,2-cyclohexane bis(urea-urethane) compounds of the formulae

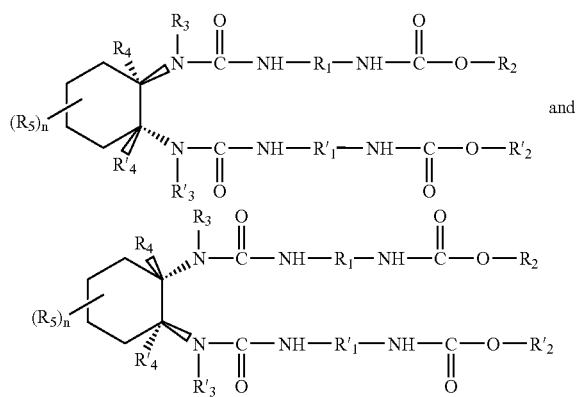

wherein $R_1$ and $R'_1$ each, independently of the other, are alkylene, arylene, arylalkylene, or alkylarylene groups, $R_2$ and $R'_2$ each, independently of the other, are alkyl, aryl, arylalkyl, or alkylaryl groups, $R_3$ and $R'_3$ each, independently of the other, are hydrogen atoms or alkyl groups, $R_4$ and $R'_4$ each, independently of the other, are hydrogen atoms, fluorine atoms, alkyl groups, or phenyl groups, n is an integer of 0, 1, 2, 3, or 4, and $R_5$ is an alkyl, aryl, arylalkyl, or alkylaryl group, or a substituent other than an alkyl, aryl, arylalkyl, or alkylaryl group, provided that at least one of $R_1$, $R'_1$, $R_2$, $R'_2$, $R_3$, $R'_3$, $R_4$, $R'_4$, or one or more of $R_5$ is an alkyl, alkylene, arylalkyl, arylalkylene, alkylaryl, or alkylarylene group containing an ethylenic unsaturation rendering the compound curable upon exposure to heat and/or actinic radiation.

Copending application U.S. Ser. No. 11/004,451, filed Dec. 4, 2004, entitled "Phase Change Inks Containing Curable Trans-1,2-cyclohexane bis(urea-urethane) Compounds," with the named inventors Rina Carlini, Eniko Toma, Peter G. Odell, and Jeffery H. Banning, the disclosure of which is totally incorporated herein by reference, discloses phase change inks comprising a phase change ink carrier and one or more curable trans-1,2-cyclohexane bis(urea-urethane) compounds of the formulae

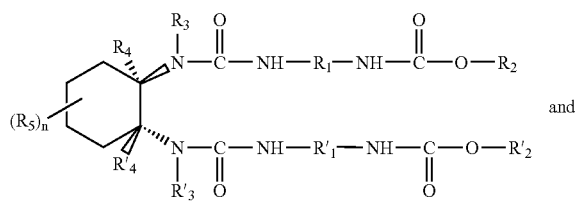

-continued

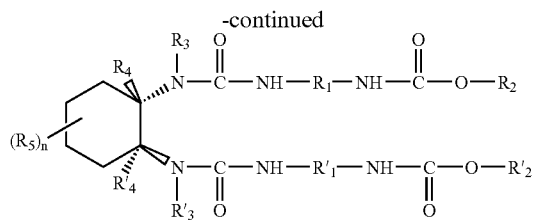

wherein $R_1$ and $R'_1$ are alkylene, arylene, arylalkylene, or alkylarylene groups, $R_2$ and $R'_2$ are alkyl, aryl, arylalkyl, or alkylaryl groups, $R_3$ and $R'_3$ are hydrogen atoms or alkyl groups, $R_4$ and $R'_4$ are hydrogen atoms, fluorine atoms, alkyl groups, or phenyl groups, n is an integer of 0, 1, 2, 3, or 4, and $R_5$ is an alkyl, aryl, arylalkyl, or alkylaryl group, or a substituent other than an alkyl, aryl, arylalkyl, or alkylaryl group, provided that at least one of $R_1$, $R'_1$, $R_2$, $R'_2$, $R_3$, $R'_3$, $R_4$, $R'_4$, or one or more of $R_5$ is an alkyl, alkylene, arylalkyl, arylalkylene, alkylaryl, or alkylarylene group containing an ethylenic unsaturation rendering the compound curable upon exposure to heat and/or actinic radiation.

Copending application U.S. Ser. No. 09/949,315, filed Sep. 7, 2001, U.S. Publication 20030079644, entitled "Aqueous Ink Compositions," with the named inventors Thomas W. Smith, David J. Luca, and Kathleen M. McGrane, the disclosure of which is totally incorporated herein by reference, discloses an aqueous ink composition comprising an aqueous liquid vehicle, a colorant, and an additive wherein, when the ink has been applied to a recording substrate in an image pattern and a substantial amount of the aqueous liquid vehicle has either evaporated from the ink image, hydrogen bonds of sufficient strength exist between the additive molecules so that the additive forms hydrogen-bonded oligomers or polymers.

Copending application U.S. Ser. No. 09/948,958, filed Sep. 7, 2001, U.S. Publication 20030105185, entitled "Phase Change Ink Compositions," with the named inventors H. Bruce Goodbrand, Thomas W. Smith, Dina Popovic, Daniel A. Foucher, and Kathleen M. McGrane, the disclosure of which is totally incorporated herein by reference, discloses a phase change ink composition comprising a colorant and an ink vehicle, the ink being a solid at temperatures less than about 50° C. and exhibiting a viscosity of no more than about 20 centipoise at a jetting temperature of no more than about 160° C., wherein at a first temperature hydrogen bonds of sufficient strength exist between the ink vehicle molecules so that the ink vehicle forms hydrogen-bonded dimers, oligomers, or polymers, and wherein at a second temperature which is higher than the first temperature the hydrogen bonds between the ink vehicle molecules are sufficiently broken that fewer hydrogen-bonded dimers, oligomers, or polymers are present in the ink at the second temperature than are present in the ink at the first temperature, so that the viscosity of the ink at the second temperature is lower than the viscosity of the ink at the first temperature.

Copending application U.S. Ser. No. 10/770,305, filed Feb. 2, 2004, U.S. Publication 20040158063, entitled "Alkylated Tetrakis(triaminotriazine) Compounds and Phase Change Inks Containing Same," with the named inventors Danielle C. Boils Boissier, Marcel P. Breton, Jule W. Thomas, Jr., Donald R. Titterington, Jeffery H. Banning, H. Bruce Goodbrand, James D. Wuest, Marie Eve Perron, Francis Monchamp, and Hugues Duval, the disclosure of which is totally incorporated herein by reference, discloses compounds of the formulae

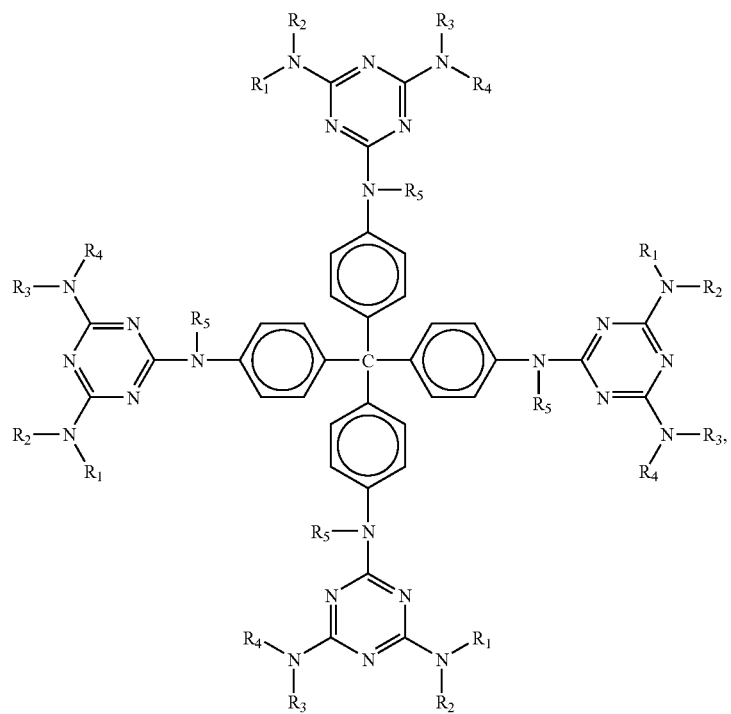
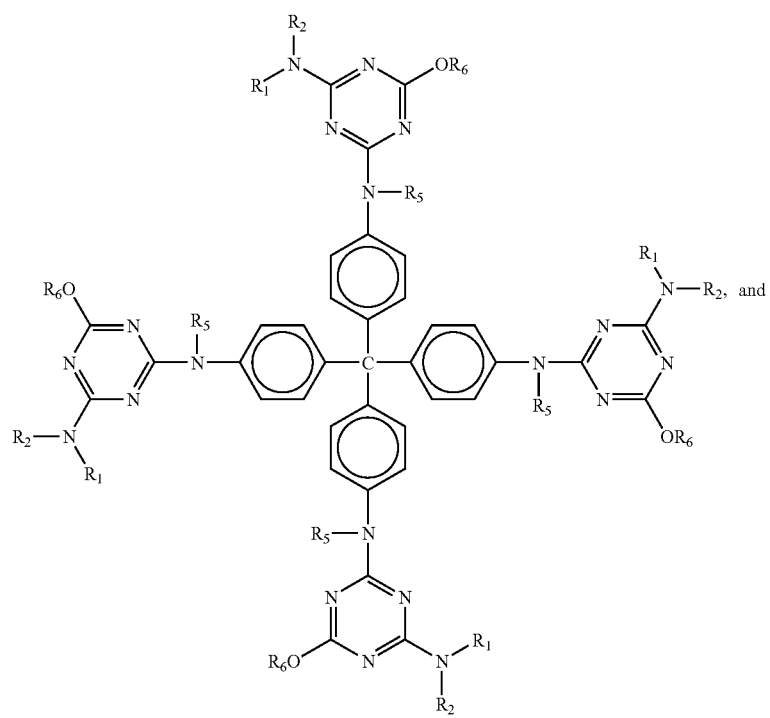

-continued

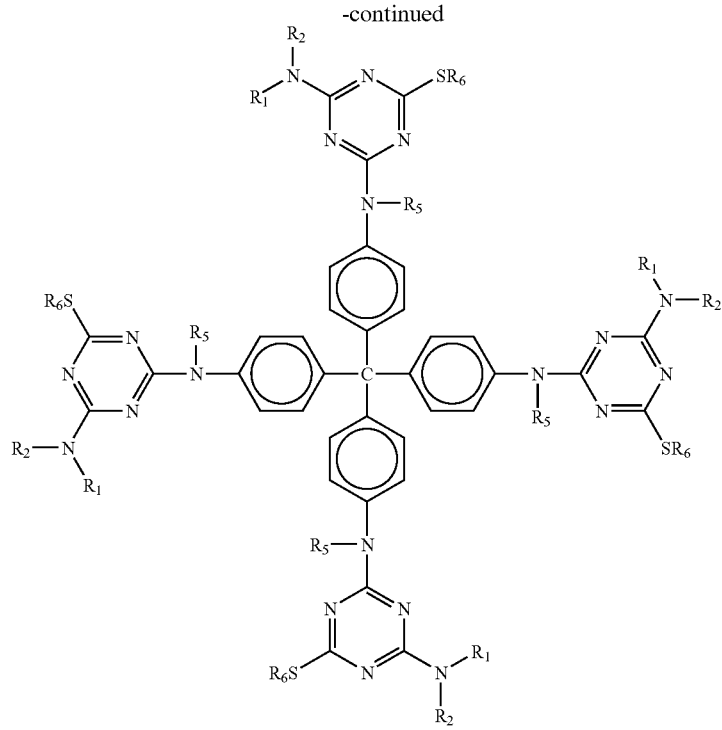

wherein, provided that at least one of $R_1$, $R_2$, $R_3$, $R_4$, $R_5$, and $R_6$ is a hydrogen atom, and provided that at least one of $R_1$, $R_2$, $R_3$, $R_4$, $R_5$, and $R_6$ is not a hydrogen atom, $R_1$, $R_2$, $R_3$, $R_4$, $R_5$, and $R_6$ each, independently of the others; is (i) a hydrogen atom, (ii) an alkyl group, (iii) an aryl group, (iv) an arylalkyl group, or (v) an alkylaryl group. Also disclosed are phase change ink compositions comprising a colorant and a phase change ink carrier comprising a material of this formula.

Copending application U.S. Ser. No. 10/235,061, filed Sep. 4, 2002, U.S. Publication 20040060474, and Copending application U.S. Ser. No. 10/794,930, filed Mar. 5, 2004, both entitled "Guanidinopyrimidinone Compounds and Phase Change Inks Containing Same," with the named inventors Danielle C. Boils-Boissier, Marcel P. Breton, Jule W. Thomas, Jr., Donald R. Titterington, Jeffery H. Banning, H. Bruce Goodbrand, James D. Wuest, Marie-Ève Perron, and Hugues Duval, the disclosure of which is totally incorporated herein by reference, discloses compounds of the formulae

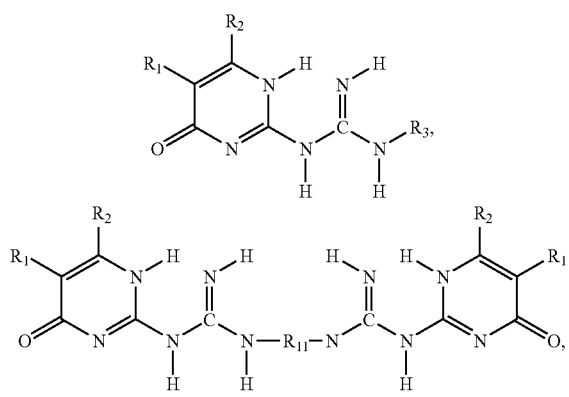

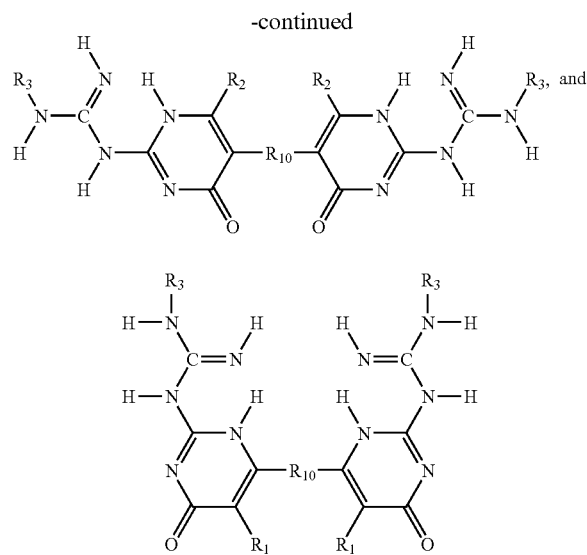

wherein, provided that at least one of $R_1$, $R_2$, and $R_3$ is not a hydrogen atom, $R_1$, $R_2$, and $R_3$ each, independently of the other, is (i) a hydrogen atom, (ii) an alkyl group, (iii) an aryl group, (iv) an arylalkyl group, or (v) an alkylaryl group, and wherein $R_1$ and $R_2$ can also be (vi) an alkoxy group, (vii) an aryloxy group, (viii) an arylalkyloxy group, (ix) an alkylaryloxy group, (x) a polyalkyleneoxy group, (xi) a polyaryleneoxy group, (xii) a polyarylalkyleneoxy group, (xiii) a polyalkylaryleneoxy group, (xiv) a silyl group, (xv) a siloxane group, (xvi) a polysilylene group, (xvii) a polysiloxane group, or (xviii) a group of the formula

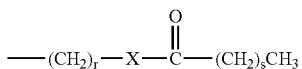

wherein r is an integer representing a number of repeat —$CH_2$— groups, wherein s is an integer representing a number of repeating —$CH_2$— groups, and wherein X is (a) a direct bond, (b) an oxygen atom, (c) a sulfur atom, (d) a group of the formula —$NR_{40}$— wherein $R_{40}$ is a hydrogen atom, an alkyl group, an aryl group, an arylalkyl group, or an alkylaryl group, or (e) a group of the formula —$CR_{50}R_{60}$— wherein $R_{50}$ and $R_{60}$ each, independently of the other, is a hydrogen atom, an alkyl group, an aryl group, an arylalkyl group, or an alkylaryl group, and $R_{10}$ and $R_{11}$ each, independently of the other, is (i) an alkylene group, (ii) an arylene group, (iii) an arylalkylene group, or (iv) an alkylarylene group, and wherein $R_{10}$ can also be (v) a polyalkyleneoxy group, (vi) a polyaryleneoxy group, (vii) a polyarylalkyleneoxy group, (viii) a polyalkylaryleneoxy group, (ix) a silylene group, (x) a siloxane group, (xi) a polysilylene group, or (xii) a polysiloxane group. Also disclosed are phase change ink compositions comprising a colorant and a phase change ink carrier comprising a material of this formula.

Copending application U.S. Ser. No. 10/235,109, filed Sep. 4, 2002, U.S. Publication 20040075723, and Copending application U.S. Ser. No. 10/810,370, filed Mar. 26, 2004, both entitled "Alkylated Urea and Triaminotriazine Compounds and Phase Change Inks Containing Same," with the named inventors Marcel P. Breton, Danielle C. Boils-Boissier, Jule W. Thomas, Jr., Donald R. Titterington, H. Bruce Goodbrand, Jeffery H. Banning, James D. Wuest, Dominic Laliberté, and Marie-Ève Perron, the disclosure of which is totally incorporated herein by reference, discloses compounds of the formulae

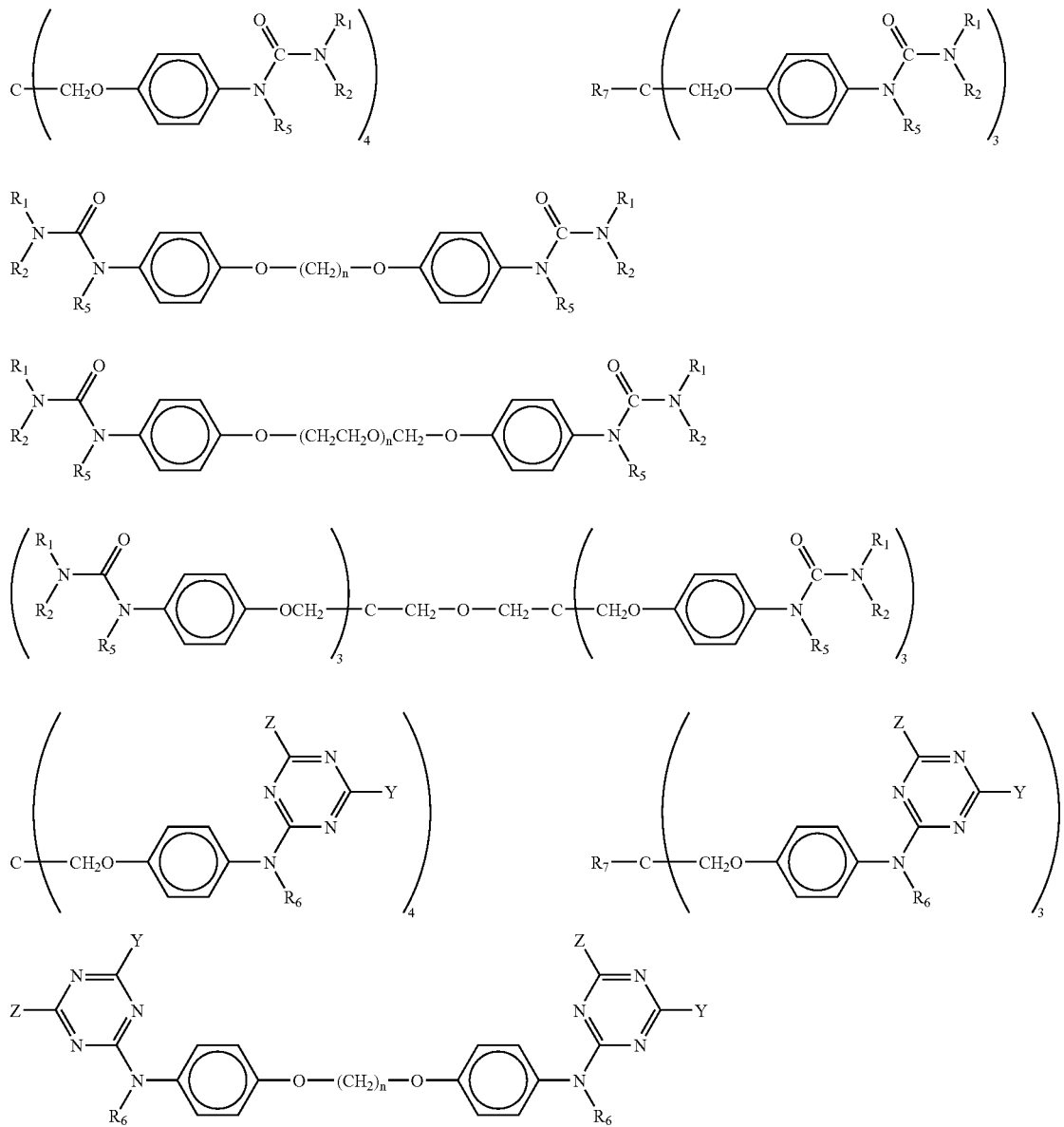

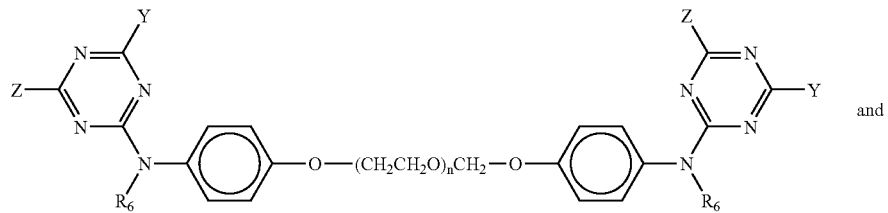

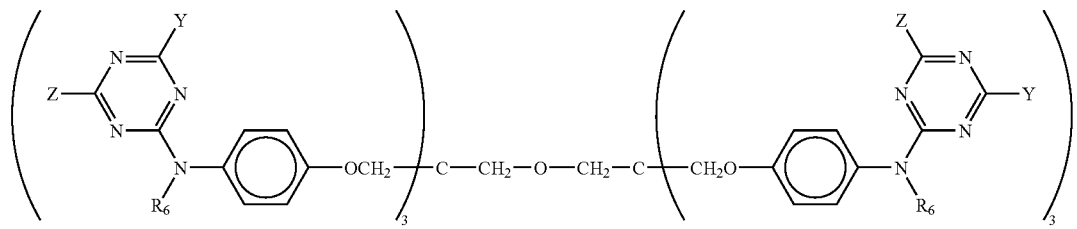

and wherein Z is a group of the formula —$OR_1$, a group of the formula —$SR_1$, or a group of the formula —$NR_1R_2$, Y is a group of the formula —$OR_3$, a group of the formula —$SR_3$, or a group of the formula —$NR_3R_4$, n is an integer representing the number of repeat —($CH_2$)— or —($CH_2CH_2O$)— units, wherein, provided that at least one of $R_1$, $R_2$, $R_3$, $R_4$, $R_5$, and $R_6$ is a hydrogen atom, provided that at least one of $R_1$, $R_2$, $R_3$, $R_4$, $R_5$, and $R_6$ is other than a hydrogen atom, and provided that at least one Z or Y within the compound is a group of the formula —$NR_1R_2$ or a group of the formula —$NR_3R_4$, $R_1$, $R_2$, $R_3$, $R_4$, $R_5$, $R_6$, and $R_7$ each, independently of the others, is (i) a hydrogen atom, (ii) an alkyl group, (iii) an aryl group, (iv) an arylalkyl group, or (v) an alkylaryl group, and wherein $R_7$ can also be (vi) an alkoxy group, (vii) an aryloxy group, (viii) an arylalkyloxy group, (ix) an alkylaryloxy group, (x) a polyalkyleneoxy group, (xi) a polyaryleneoxy group, (xii) a polyarylalkyleneoxy group, (xiii) a polyalkylaryleneoxy group, (xiv) a silyl group, (xv) a siloxane group, (xvi) a polysilylene group, (xvii) a polysiloxane group, or (xviii) a group of the formula

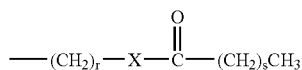

wherein r is an integer representing a number of repeat —$CH_2$— groups, wherein s is an integer representing a number of repeating —$CH_2$— groups, and wherein X is (a) a direct bond, (b) an oxygen atom, (c) a sulfur atom, (d) a group of the formula —$NR_{40}$— wherein $R_{40}$ is a hydrogen atom, an alkyl group, an aryl group, an arylalkyl group, or an alkylaryl group, or (e) a group of the formula —$CR_{50}R_{60}$— wherein $R_{50}$ and $R_{60}$ each, independently of the other, is a hydrogen atom, an alkyl group, an aryl group, an arylalkyl group, or an alkylaryl group, and wherein $R_6$ can also be

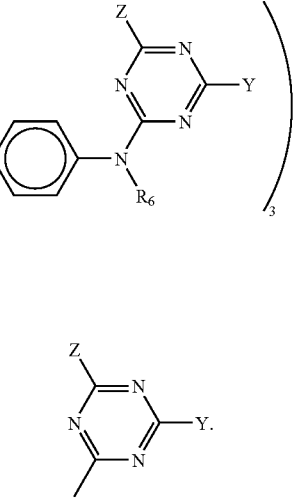

Also disclosed are phase change ink compositions comprising a colorant and a phase change ink carrier comprising a material of this formula.

Copending application U.S. Ser. No. 10/235,125, filed Sep. 4, 2002, U.S. Publication 20040065227, entitled "Phase Change Inks Containing Gelator Additives," with the named inventors Marcel P. Breton, Danielle C. Boils-Boissier, Donald R. Titterington, Jule W. Thomas, Jr., Jeffery H. Banning, Christy Bedford, and James D. Wuest, the disclosure of which is totally incorporated herein by reference, discloses a phase change ink composition comprising an ink vehicle, a colorant, and a nonpolymeric organic gelator selected from the group consisting of anthracene-based compounds, steroid compounds, partially fluorinated high molecular weight alkanes, high molecular weight alkanes with exactly one hetero atom, chiral tartrate compounds, chiral butenolide-based compounds, bis-urea compounds, guanines, barbiturates, oxamide compounds, ureidopyrimidone compounds, and mixtures thereof, said organic gelator being present in the ink in an amount of no more than about 20 percent by weight of the ink, said ink having a melting point at or below which the ink is a solid, said ink having a gel point at or above which the ink is a liquid, and said ink exhibiting a gel state between the melting point and the gel point, said ink exhibiting reversible transitions between the solid state and the gel state upon heating and cooling, said ink exhibiting reversible transitions between the gel state and the liquid state upon heating and cooling, said melting point being greater than about 35° C., said gel point being greater than said melting point. Also

BACKGROUND

Disclosed herein are processes for preparing bis(urea-urethane) compounds. One embodiment is directed to a process for preparing bis(urea-urethane) compounds of the formula

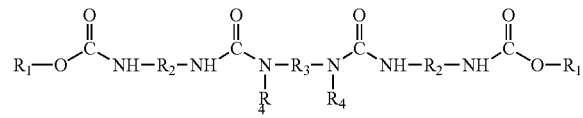

wherein $R_1$ is an alkyl group, an aryl group, an arylalkyl group, or an alkylaryl group, $R_2$ is an alkylene group, an arylene group, an arylalkylene group, or an alkylarylene group, $R_3$ is an alkylene group, an arylene group, an arylalkylene group, or an alkylarylene group, and $R_4$ is a hydrogen atom or an alkyl group, said process comprising: (1) first bring to a reaction temperature of from about 20 to about 125° C. a reaction mixture comprising a monoalcohol reactant of the formula $R_1$—OH and a diisocyanate reactant of the formula OCN—$R_2$—NCO, said monoalcohol being present in an amount of from about 0.8 to about 1.2 moles of monoalcohol per every one mole of diisocyanate, said monoalcohol and said diisocyanate reactants being admixed in a solvent, said reactants and said solvent being present in relative amounts of at least about 1 milliliter of solvent per every 1 millimole of diisocyanate, said reaction temperature continuing until reaction between the monoalcohol and the diisocyanate is complete; and (2) subsequent to step (1), adding to the reaction mixture a diamine of the formula

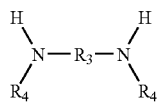

without isolating the reaction product of step (1), thereby forming a compound of the formula

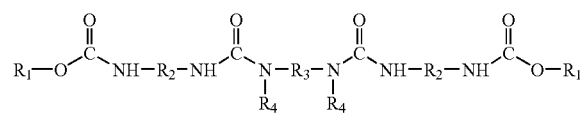

in desirably high yield and high purity.

"Cyclic Bis-Urea Compounds as Gelators for Organic Solvents," J. van Esch et al., Chem. Eur. J. 1999, 5, No. 3, pp. 937-950, the disclosure of which is totally incorporated herein by reference, discloses the study of the gelation properties of bis-urea compounds derived from optically pure trans-1,2-diaminocyclohexane and 1,2-diaminobenzene, with pendant aliphatic, aromatic, or ester groups, as well as the structure of the resulting gels.

"The Design of Organic Gelators Based on a Family of Bis-Ureas," R. E. Meléndez et al., Mat. Res. Soc. Symp. Proc. 2000, 604, pp. 335-340, the disclosure of which is totally incorporated herein by reference, discloses a study of the organogelation properties of a family of bis-ureas.

"Formation of Organogels by Intermolecular Hydrogen Bonding Between Ureylene Segment," K. Hanabusa et al., Chem. Lett. 1996 pp. 885-886, the disclosure of which is totally incorporated herein by reference, discloses low molecular weight compounds having ureylene segment causing physical gelation in organic solvents. The main driving force for gelation was intermolecular hydrogen bonding between ureylene units.

"Low Molecular Weight Gelators for Organic Solvents," J. van Esch et al., in Supramolecular Science: Where Is It and Where It Is Going, R. Ungaro and E. Dalcanale, Eds., 1999, Netherlands: Kluwer Academic Publishers, pp. 233-259, the disclosure of which is totally incorporated herein by reference, discloses the gelation of solvents by organogelators.

"Organogels and Low Molecular Mass Organic Gelators," D. J. Abdallah and R. G. Weiss, Adv. Mater. 2000, 12, No. 17, September 1, pp. 1237-1247, the disclosure of which is totally incorporated herein by reference, discloses the stepwise simplification of low molecular-mass organic gelator structures and the development of methods to determine their packing in organogels at the micrometer-to-angstrom distance regimes, as well as an overview of current and potential applications for these materials.

"Remarkable Stabilization of Self-Assembled Organogels by Polymerization," M. de Loos et al., J. Am. Chem. Soc. 1997, 119, 12675-12676, the disclosure of which is totally incorporated herein by reference, discloses studies of polymerizable bis(amido)cyclohexane and bis(ureido)cyclohexane derivatives, investigating their gelating capacity for organic solvents.

"Low-molecular weight organogelators," P. Terech, in Specialist Surfactants, I. D. Robb, Ed., 1997, London: Chapman & Hall, pp. 208-68, the disclosure of which is totally incorporated herein by reference, discloses a special class of surfactants which have the ability to form viscoelastic fluids or solid-like materials in organic solvents at concentrations lower than about 2 percent.

"New Functional Materials Based on Self-Assembling Organogels: From Serendipity Towards Design," J. H. van Esch and B. L. Feringa, Angew. Chem. Int. Ed. 2000, 39, No. 13, pp. 2263-2266, the disclosure of which is totally incorporated herein by reference, discloses a review of developments in the field of organogels.

"Synthesis and Self-Assembling Properties of Polymerizable Organogelators," G. Wang and A. D. Hamilton, Chem. Eur. J. 2002, 8, No. 8, pp. 1954-1961, the disclosure of which is totally incorporated herein by reference, discloses the development of a family of polymerizable urea derivatives that are gelators for organic solvents.

"Low Molecular Mass Gelators of Organic Liquids and the Properties of their Gels," P. Terech and R. G. Weiss, Chem. Rev. 1997, 97 pp. 3133-3159, the disclosure of which is totally incorporated herein by reference, discloses a review of the properties of thermally-reversible viscoelastic liquidlike or solidlike organogels comprising an organic liquid and low concentrations of relatively low molecular mass gelator molecules.

"Towards a Phenomenological Definition of the Term 'Gel'," K. Amdal et al., Polymer Gels and Networks, 1993, 1, pp. 5-17, the disclosure of which is totally incorporated herein by reference, discusses existing definitions of the term "gel" and proposes specific uses of the term.

PCT Patent Publication WO 03/084508 and European Patent Publication EP 1 350 507 (Friesen et al.), the disclosures of each of which are totally incorporated herein by reference, disclose delivery vehicles for delivering a substance of interest to a predetermined site, said vehicle comprising said substance and a means for inducing availability of at least one compartment of said vehicle toward the exterior, thereby allowing access of said substance to the exterior of said vehicle at said predetermined site. The invention is further concerned with uses of said vehicle and methods for preparing it.

PTC Patent Publication WO 03/040135 (Dowle et al.), the disclosure of which is totally incorporated herein by reference, discloses compounds of the formula

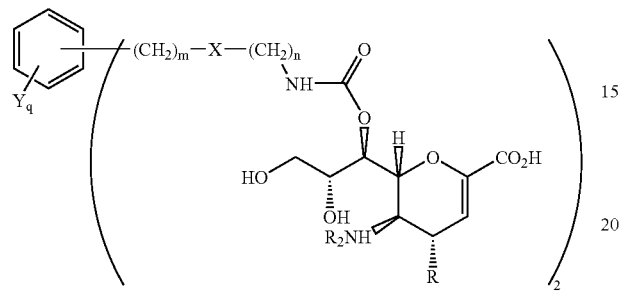

in which R is an amino or guanidino group, $R_2$ is acetyl or trifluoroacetyl, X is CONH, $SO_2NH$, NHCO, or NHCONH, m is either 0 or 1, n is an integer from 2 to 6, q is an integer from 0 to 3, and Y is hydrogen or an aromatic substituent, or a pharmaceutically acceptable derivative thereof. Also disclosed are methods for their preparation, pharmaceutical formulations containing them, and their use in the prevention or treatment of a viral infection.

PTC Patent Publication WO 00/55149 and U.S. Pat. No. 6,548,476 (Wu et al.), the disclosures of each of which are totally incorporated herein by reference, disclose dimeric compounds, methods for their preparation, pharmaceutical formulations thereof, and their use as antiviral agents. The compounds are particularly useful against influenza virus. In particular the references disclose a dimeric compound which comprises two neuraminidase binding groups attached to a spacer or linking group. Preferably the dimeric molecule comprises two neuraminidase-binding neuraminic acid (sialic acid) or cyclopentyl or cyclohexenyl carboxylic acid derivatives covalently attached to a common spacer group. Pharmaceutical compositions and methods of treatment, prophylaxis and diagnosis are disclosed and claimed.

U.S. Patent Publication 20010044553 (Kabashima et al.), the disclosure of which is totally incorporated herein by reference, discloses a urea-urethane compound having one or more urea groups and one or more urethane groups in the molecular structure, the number of said urea groups (A) and the number of said urethane groups (B) satisfying the following numerical formula: $10 \geqq (A+B) \geqq 3$ wherein each of A and B is an integer of 1 or more.

European Patent Publication EP 1 048 681 and U.S. Pat. No. 6,420,466 (Haubennestel et al.), the disclosures of each of which are totally incorporated herein by reference, disclose a process for preparing a solution that is active as a thixotropic agent and contains urea urethanes, in which monohydroxyl compounds are reacted with an excess of toluene diisocyanate, the unreacted portion of the toluene diisocyanate is removed from the reaction mixture, and the monosiocyanate adduct obtained is further reacted with diarines in the presence of a lithium salt to form urea urethanes. The invention also relates to the use of the solution for imparting thixotropic properties to coating compounds.

Japanese Patent Publication JP 10310633, the disclosure of which is totally incorporated herein by reference, discloses a cationic curing catalyst composition improved in stability during storage at room temperature or above and suppressed in increase in viscosity, using at least one stabilizer selected from the compounds containing a urethane bond, an amide bond, a urea bond and a carbodiimide group in the molecule and a dialkylaminopyridine compound or a proton acid compound.

European Patent Publication EP0 056 153 and U.S. Pat. No. 4,384,102 (Rasshofer et al.), the disclosures of each of which are totally incorporated herein by reference, disclose compounds having both s-triazine units and epoxide groups present that are prepared by reacting an epoxide containing an isocyanate-reactive group with a triisocyanate corresponding to the formula 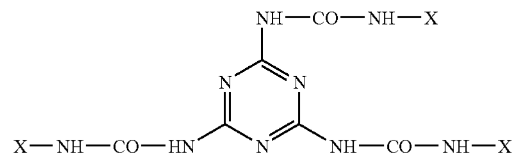 in which X is as defined therein. These reactants are used in quantities such that the equivalent ratio of isocyanate groups to isocyanate-reactive groups is maintained at less than or equal to 1 to 1. The compounds thus produced are particularly useful as reactive cross-linkers in the production of polyurethanes and polyepoxides.

European Patent Publication EP 0 160 402 and U.S. Pat. No. 4,566,981 (Howells), the disclosures of each of which are totally incorporated herein by reference, disclose cationic and non-ionic fluorochemicals, mixtures of cationic and non-ionic fluorochemicals, blends of the mixtures with fluorochemical poly(oxyalkylenes), and compositions of the fluorochemicals with hydrocarbon nonionic surfactants. These fluorochemicals and compositions, in dispersions, emulsions and microemulsions, may be applied to porous fibrous substrates to give oil and water repellency and soil resistance.

Japanese Patent Publication JP 59030919, the disclosure of which is totally incorporated herein by reference, discloses a method to prevent the bad influence of a treatment on spinning properties and drawing properties of synthetic yarn, by providing undrawn yarn of melt spinning with a spinning oil, applying a specific treatment to it, drawing and heat-treating it. The undrawn yarn which is prepared by melt spinning and cooled is provided with a spinning oil by the oil applicator, coated with a treatment by the treatment applicator, sent through the taking up roller and the drawing rollers, and wound around the winder. The treatment is a compound shown by the formula $(R_f—A—B_1—CONH—X—NHCO—B_2—)_nY$ ($R_f$ is 4-16 C perfluoroalkyl; A is $—(CH_2)_{x1}—$, $CON(R_1)—(CH_2)_{x2}—$, or $SO_2N(R_1)—(CH_2)_{x2}—$; x1 is 1-20 integer; x2 is 1-12 integer; $R_1$ is H, or 1-6 C alkyl; $B_1$ and $B_2$ are —O—, —S—, or $—N(R_2)—$; $R_2$ is H, or 1-4 C alkyl; X is bifunctional organic group; Y is polyfunctional organic group; n is 2-10 integer) and its pickup is 0.03-2.0 wt %.

Methods for preparing bis(urea-urethane) compounds are known. Known methods, however, result in products generated at low yields and in the generation of many byproducts and intermediates as well as the desired product. In addition, known methods require many steps and the isolation of intermediate products. A need remains for methods for preparing bis(urea-urethane) compounds that can be performed in a single pot. In addition, a need remains for methods for preparing bis(urea-urethane) compounds that results in production of the desired product in high yield. Further, a need remains for methods for preparing bis(urea-urethane) compounds that enables production of the desired product in high purity. Additionally, a need remains for methods for preparing bis(urea-urethane) compounds that requires no isolation or treatment of intermediate products. There is also a need for methods for preparing bis(urea-urethane) compounds that requires no use of excess starting reactants.

SUMMARY

Disclosed herein is a process for preparing bis(urea-urethane) compounds of the formula

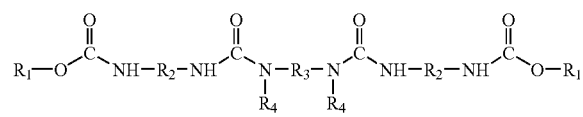

wherein $R_1$ is an alkyl group, an aryl group, an arylalkyl group, or an alkylaryl group, $R_2$ is an alkylene group, an arylene group, an arylalkylene group, or an alkylarylene group, $R_3$ is an alkylene group, an arylene group, an arylalkylene group, or an alkylarylene group, and $R_4$ is a hydrogen atom or an alkyl group, said process comprising: (1) first bring to a reaction temperature of from about 20 to about 125° C. a reaction mixture comprising a monoalcohol reactant of the formula $R_1$—OH and a diisocyanate reactant of the formula OCN—$R_2$—NCO, said monoalcohol being present in an amount of from about 0.8 to about 1.2 moles of monoalcohol per every one mole of diisocyanate, said monoalcohol and said diisocyanate reactants being admixed in a solvent, said reactants and said solvent being present in relative amounts of at least about 1 milliliter of solvent per every 1 millimole of diisocyanate, said reaction temperature continuing until reaction between the monoalcohol and the diisocyanate is complete; and (2) subsequent to step (1), adding to the reaction mixture a diamine of the formula

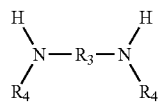

without isolating the reaction product of step (1), thereby forming a compound of the formula

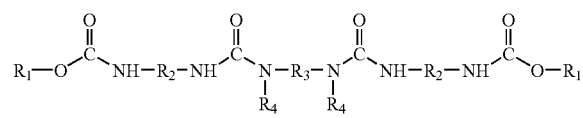

in desirably high yield and high purity.

DETAILED DESCRIPTION

The bis(urea-urethane) compounds are of the formula

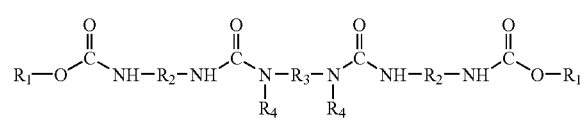

wherein $R_1$ is (i) an alkyl group (including linear, branched, saturated, unsaturated, cyclic, substituted, and unsubstituted alkyl groups, and wherein hetero atoms, such as oxygen, nitrogen, sulfur, silicon, phosphorus, boron, and the like either may or may not be present in the alkyl group), in one embodiment with at least 1 carbon atom, in another embodiment with at least about 4 carbon atoms, and in yet another embodiment with at least about 10 carbon atoms, and in one embodiment with no more than about 100 carbon atoms, in another embodiment with no more than about 60 carbon atoms, and in yet another embodiment with no more than about 30 carbon atoms, although the number of carbon atoms can be outside of these ranges, including (but not limited to) (1) linear saturated unsubstituted aliphatic groups containing no hetero atoms, (2) branched saturated unsubstituted aliphatic groups containing no hetero atoms, (3) cyclic saturated unsubstituted aliphatic groups containing no hetero atoms, (4) aliphatic groups containing both cyclic and acyclic portions, said aliphatic groups being saturated, unsubstituted, and containing no hetero atoms, (5) linear ethylenically unsaturated unsubstituted aliphatic groups containing no hetero atoms, (6) branched ethylenically unsaturated unsubstituted aliphatic groups containing no hetero atoms, (7) cyclic ethylenically unsaturated unsubstituted aliphatic groups containing no hetero atoms, (8) aliphatic groups containing both cyclic and acyclic portions, said aliphatic groups being ethylenically unsaturated, unsubstituted, and containing no hetero atoms, (9) linear saturated substituted aliphatic groups containing no hetero atoms, (10) branched saturated substituted aliphatic groups containing no hetero atoms, (11) cyclic saturated substituted aliphatic groups containing no hetero atoms, (12) aliphatic groups containing both cyclic and acyclic portions, said aliphatic groups being saturated, substituted, and containing no hetero atoms, (13) linear ethylenically unsaturated substituted aliphatic groups containing no hetero atoms, (14) branched ethylenically unsaturated substituted aliphatic groups containing no hetero atoms, (15) cyclic ethylenically unsaturated substituted aliphatic groups containing no hetero atoms, (16) aliphatic groups containing both cyclic and acyclic portions, said aliphatic groups being ethylenically unsaturated, substituted, and contain no hetero atoms, (17) linear saturated unsubstituted aliphatic groups containing hetero atoms, (18) branched saturated unsubstituted aliphatic groups containing hetero atoms, (19) cyclic saturated unsubstituted aliphatic groups containing hetero atoms, (20) aliphatic groups containing both cyclic and acyclic portions, said aliphatic groups being saturated, unsubstituted, and containing hetero atoms, (21) linear ethylenically unsaturated unsubstituted aliphatic groups containing hetero atoms, (22) branched ethylenically unsaturated unsubstituted aliphatic groups containing hetero atoms, (23) cyclic ethylenically unsaturated unsubstituted aliphatic groups containing hetero atoms, (24) aliphatic groups containing both cyclic and acyclic portions, said aliphatic groups being ethylenically unsaturated, unsubstituted, and containing hetero atoms, (25) linear saturated substituted aliphatic groups containing hetero atoms, (26) branched saturated substituted aliphatic groups containing hetero atoms, (27) cyclic saturated substituted aliphatic groups containing hetero atoms, (28) aliphatic groups containing both cyclic and acyclic portions, said aliphatic groups being saturated, substituted, and containing hetero atoms, (29) linear ethylenically unsaturated substituted aliphatic groups containing hetero atoms, (30) branched ethylenically unsaturated substituted aliphatic groups containing hetero atoms, (31) cyclic ethylenically unsaturated substituted aliphatic groups containing hetero atoms, and (32) aliphatic groups containing both cyclic and acyclic portions, said aliphatic groups being ethylenically unsaturated, substituted, and containing hetero atoms, (ii) an aryl group (including substituted and unsubstituted aryl groups, and wherein hetero atoms, such as oxygen, nitrogen, sulfur, silicon, phosphorus, boron, and the like either may or may not be present in the aryl group), in one embodiment with at least about 5 carbon atoms, and in another embodiment with at least about 6 carbon atoms, and in one embodiment with no more than about 18 carbon atoms, in another embodiment with no more than about 12 carbon atoms, and in yet another embodiment with no more than about 6 carbon atoms, although the number of carbon atoms can be outside of these ranges, (iii) an arylalkyl group (including substituted and unsubstituted arylalkyl groups, and wherein hetero atoms, such as oxygen, nitrogen, sulfur, silicon, phosphorus, boron, and the like either may or may not be present in either the aryl or the alkyl portion of the arylalkyl group), in one embodiment with at least about 6 carbon atoms, and in another embodiment with at least about 7 carbon atoms, and in one embodiment with no more than about 100 carbon atoms, in another embodiment with no more than about 60 carbon atoms, and in yet another embodiment with no more than about 30 carbon atoms, although the number of carbon atoms can be outside of these ranges, such as benzyl or the like, or (iv) an alkylaryl group (including substituted and unsubstituted alkylaryl groups, and wherein hetero atoms, such as oxygen, nitrogen, sulfur, silicon, phosphorus, boron, and the like either may or may not be present in either the aryl or the alkyl portion of the alkylaryl group), in one embodiment with at least about 6 carbon atoms, and in another embodiment with at least about 7 carbon atoms, and in one embodiment with no more than about 100 carbon atoms, in another embodiment with no more than about 60 carbon atoms, and in yet another embodiment with no more than about 30 carbon atoms, although the number of carbon atoms can be outside of these ranges, such as tolyl or the like, $R_2$ is (i) an alkylene group (including linear, branched, saturated, unsaturated, cyclic, substituted, and unsubstituted alkylene groups, and wherein hetero atoms, such as oxygen, nitrogen, sulfur, silicon, phosphorus, boron, and the like either may or may not be present in the alkylene group), in one embodiment with at least about 2 carbon atoms, in another embodiment with at least about 4 carbon atoms, and in yet another embodiment with at least about 6 carbon atoms, and in one embodiment with no more than about 100 carbon atoms, in another embodiment with no more than about 60 carbon atoms, and in yet another embodiment with no more than about 30 carbon atoms, although the number of carbon atoms can be outside of these ranges, including (but not limited to) (1) linear saturated unsubstituted aliphatic groups containing no hetero atoms, (2) branched saturated unsubstituted aliphatic groups containing no hetero atoms, (3) cyclic saturated unsubstituted aliphatic groups containing no hetero atoms, (4) aliphatic groups containing both cyclic and acyclic portions, said aliphatic groups being saturated, unsubstituted, and containing no hetero atoms, (5) linear ethylenically unsaturated unsubstituted aliphatic groups containing no hetero atoms, (6) branched ethylenically unsaturated unsubstituted aliphatic groups containing no hetero atoms, (7) cyclic ethylenically unsaturated unsubstituted aliphatic groups containing no hetero atoms, (8) aliphatic groups containing both cyclic and acyclic portions, said aliphatic groups being ethylenically unsaturated, unsubstituted, and containing no hetero atoms, (9) linear saturated substituted aliphatic groups containing no hetero atoms, (10) branched saturated substituted aliphatic groups containing no hetero atoms, (11) cyclic saturated substituted aliphatic groups containing no hetero atoms, (12) aliphatic groups containing both cyclic and acyclic portions, said aliphatic groups being saturated, substituted, and containing no hetero atoms, (13) linear ethylenically unsaturated substituted aliphatic groups containing no hetero atoms, (14) branched ethylenically unsaturated substituted aliphatic groups containing no hetero atoms, (15) cyclic ethylenically unsaturated substituted aliphatic groups containing no hetero atoms, (16) aliphatic groups containing both cyclic and acyclic portions, said aliphatic groups being ethylenically unsaturated, substituted, and contain no hetero atoms, (17) linear saturated unsubstituted aliphatic groups containing hetero atoms, (18) branched saturated unsubstituted aliphatic groups containing hetero atoms, (19) cyclic saturated unsubstituted aliphatic groups containing hetero atoms, (20) aliphatic groups containing both cyclic and acyclic portions, said aliphatic groups being saturated, unsubstituted, and containing hetero atoms, (21) linear ethylenically unsaturated unsubstituted aliphatic groups containing hetero atoms, (22) branched ethylenically unsaturated unsubstituted aliphatic groups containing hetero atoms, (23) cyclic ethylenically unsaturated unsubstituted aliphatic groups containing hetero atoms, (24) aliphatic groups containing both cyclic and acyclic portions, said aliphatic groups being ethylenically unsaturated, unsubstituted, and containing hetero atoms, (25) linear saturated substituted aliphatic groups containing hetero atoms, (26) branched saturated substituted aliphatic groups containing hetero atoms, (27) cyclic saturated substituted aliphatic groups containing hetero atoms, (28) aliphatic groups containing both cyclic and acyclic portions, said aliphatic groups being saturated, substituted, and containing hetero atoms, (29) linear ethylenically unsaturated substituted aliphatic groups containing hetero atoms, (30) branched ethylenically unsaturated substituted aliphatic groups containing hetero atoms, (31) cyclic ethylenically unsaturated substituted aliphatic groups containing hetero atoms, and (32) aliphatic groups containing both cyclic and acyclic portions, said aliphatic groups being ethylenically unsaturated, substituted, and containing hetero atoms, (ii) an arylene group (including substituted and unsubstituted arylene groups, and wherein hetero atoms, such as oxygen, nitrogen, sulfur, silicon, phosphorus, boron, and the like either may or may not be present in the arylene group), in one embodiment with at least about 5 carbon atoms, and in another embodiment with at least about 6 carbon atoms, and in one embodiment with no more than about 18 carbon atoms, in another embodiment with no more than about 12 carbon atoms, and in yet another embodiment with no more than about 6 carbon atoms, although the number of carbon atoms can be outside of these ranges, (iii) an arylalkylene group (including substituted and unsubstituted arylalkylene groups, and wherein hetero atoms, such as oxygen, nitrogen, sulfur, silicon, phosphorus, boron, and the like either may or may not be present in either the aryl or the alkyl portion of the arylalkylene group), in one embodiment with at least about 6 carbon atoms, and in another embodiment with at least about 7 carbon atoms, and in one embodiment with no more than about 100 carbon atoms, in another embodiment with no more than about 60 carbon atoms, and in yet another embodiment with no more than about 30 carbon atoms, although the number of carbon atoms can be outside of these ranges, such as benzylene or the like, including (a) arylalkylene groups wherein both the aryl and the alkyl portions form the linkage between the two —NH— groups, such as

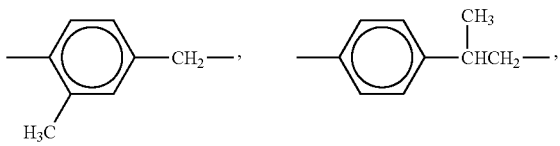

and the like, and (b) arylalkylene groups wherein only the alkyl portion forms the linkage between the two —NH— groups, such as

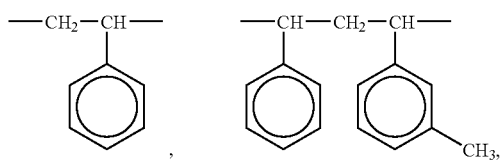

and the like, or (iv) an alkylarylene group (including substituted and unsubstituted alkylarylene groups, and wherein hetero atoms, such as oxygen, nitrogen, sulfur, silicon, phosphorus, boron, and the like either may or may not be present in either the aryl or the alkyl portion of the alkylarylene group), in one embodiment with at least about 6 carbon atoms, and in another embodiment with at least about 7 carbon atoms, and in one embodiment with no more than about 100 carbon atoms, in another embodiment with no more than about 60 carbon atoms, and in yet another embodiment with no more than about 30 carbon atoms, although the number of carbon atoms can be outside of these ranges, such as tolylene or the like, including (a) alkylarylene groups wherein both the alkyl and the aryl portions form the linkage between the two —NH— groups, such as

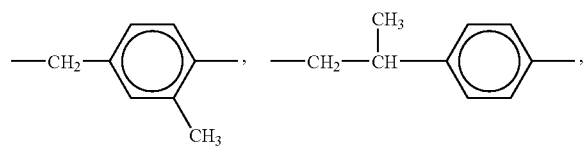

and the like, and (b) alkylarylene groups wherein only the aryl portion forms the linkage between the two —NH— groups, such as

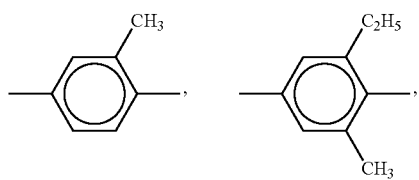

and the like, $R_3$ is (i) an alkylene group (including linear, branched, saturated, unsaturated, cyclic, substituted, and unsubstituted alkylene groups, and wherein hetero atoms, such as oxygen, nitrogen, sulfur, silicon, phosphorus, boron, and the like either may or may not be present in the alkylene group), in one embodiment with at least about 2 carbon atoms, in another embodiment with at least about 4 carbon atoms, in yet another embodiment with at least about 6 carbon atoms, in still another embodiment with at least about 8 carbon atoms, in another embodiment with at least about 10 carbon atoms, in yet another embodiment with at least about 12 carbon atoms, in still another embodiment with at least about 14 carbon atoms, in another embodiment with at least about 16 carbon atoms, in yet another embodiment with at least about 18 carbon atoms, in still another embodiment with about 20 carbon atoms, in another embodiment with at least about 22 carbon atoms, in yet another embodiment with at least about 24 carbon atoms, in still another embodiment with about 26 carbon atoms, in another embodiment with at least about 28 carbon atoms, in yet another embodiment with at least about 30 carbon atoms, in still another embodiment with about 32 carbon atoms, in another embodiment with at least about 34 carbon atoms, and in yet another embodiment with at least about 36 carbon atoms, and in one embodiment with no more than about 200 carbon atoms, in another embodiment with no more than about 100 carbon atoms, and in yet another embodiment with no more than about 50 carbon atoms, although the number of carbon atoms can be outside of these ranges, including (but not limited to) (1) linear saturated unsubstituted aliphatic groups containing no hetero atoms, (2) branched saturated unsubstituted aliphatic groups containing no hetero atoms, (3) cyclic saturated unsubstituted aliphatic groups containing no hetero atoms, (4) aliphatic groups containing both cyclic and acyclic portions, said aliphatic groups being saturated, unsubstituted, and containing no hetero atoms, (5) linear ethylenically unsaturated unsubstituted aliphatic groups containing no hetero atoms, (6) branched ethylenically unsaturated unsubstituted aliphatic groups containing no hetero atoms, (7) cyclic ethylenically unsaturated unsubstituted aliphatic groups containing no hetero atoms, (8) aliphatic groups containing both cyclic and acyclic portions, said aliphatic groups being ethylenically unsaturated, unsubstituted, and containing no hetero atoms, (9) linear saturated substituted aliphatic groups containing no hetero atoms, (10) branched saturated substituted aliphatic groups containing no hetero atoms, (11) cyclic saturated substituted aliphatic groups containing no hetero atoms, (12) aliphatic groups containing both cyclic and acyclic portions, said aliphatic groups being saturated, substituted, and containing no hetero atoms, (13) linear ethylenically unsaturated substituted aliphatic groups containing no hetero atoms, (14) branched ethylenically unsaturated substituted aliphatic groups containing no hetero atoms, (15) cyclic ethylenically unsaturated substituted aliphatic groups containing no hetero atoms, (16) aliphatic groups containing both cyclic and acyclic portions, said aliphatic groups being ethylenically unsaturated, substituted, and contain no hetero atoms, (17) linear saturated unsubstituted aliphatic groups containing hetero atoms, (18) branched saturated unsubstituted aliphatic groups containing hetero atoms, (19) cyclic saturated unsubstituted aliphatic groups containing hetero atoms, (20) aliphatic groups containing both cyclic and acyclic portions, said aliphatic groups being saturated, unsubstituted, and containing hetero atoms, (21) linear ethylenically unsaturated unsubstituted aliphatic groups containing hetero atoms, (22) branched ethylenically unsaturated unsubstituted aliphatic groups containing hetero atoms, (23) cyclic ethylenically unsaturated unsubstituted aliphatic groups containing hetero atoms, (24) aliphatic groups containing both cyclic and acyclic portions, said aliphatic groups being ethylenically unsaturated, unsubstituted, and containing hetero atoms, (25) linear saturated substituted aliphatic groups containing hetero atoms, (26) branched saturated substituted aliphatic groups containing hetero atoms, (27) cyclic saturated substituted aliphatic groups containing hetero atoms, (28) aliphatic groups containing both cyclic and acyclic portions, said aliphatic groups being saturated, substituted, and containing hetero atoms, (29) linear ethylenically unsaturated substituted aliphatic groups containing hetero atoms, (30) branched ethylenically unsaturated substituted aliphatic groups containing hetero atoms, (31) cyclic ethylenically unsaturated substituted aliphatic groups containing hetero atoms, and (32) aliphatic groups containing both cyclic and acyclic portions, said aliphatic groups being ethylenically unsaturated, substituted, and containing hetero atoms, (ii) an arylene group (including substituted and unsubstituted arylene groups, and wherein hetero atoms, such as oxygen, nitrogen, sulfur, silicon, phosphorus, boron, and the like either may or may not be present in the arylene group), in one embodiment with at least about 5 carbon atoms, and in another embodiment with at least about 6 carbon atoms, and in one embodiment with no more than about 50 carbon atoms, in another embodiment with no more than about 25 carbon atoms, and in yet another embodiment with no more than about 18 carbon atoms, although the number of carbon atoms can be outside of these ranges, (iii) an arylalkylene group (including substituted and unsubstituted arylalkylene groups, and wherein hetero atoms, such as oxygen, nitrogen, sulfur, silicon, phosphorus, boron, and the like either may or may not be present in either the aryl or the alkyl portion of the arylalkylene group), in one embodiment with at least about 6 carbon atoms, and in another embodiment with at least about 7 carbon atoms, and in one embodiment with no more than about 200 carbon atoms, in another embodiment with no more than about 100 carbon atoms, and in yet another embodiment with no more than about 50 carbon atoms, although the number of carbon atoms can be outside of these ranges, such as benzylene or the like, including (a) arylalkylene groups wherein both the aryl and the alkyl portions form the linkage between the —NR$_4$— groups, such as

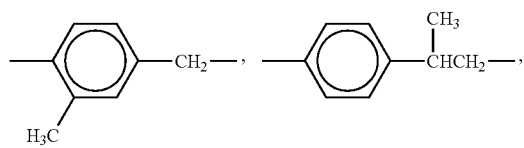

and the like, and (b) arylalkylene groups wherein only the alkyl portion forms the linkage between the —NR$_4$— groups, such as

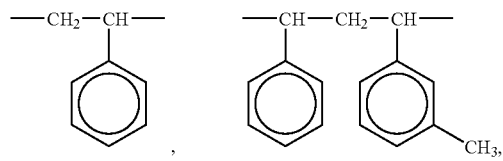

and the like, or (iv) an alkylarylene group (including substituted and unsubstituted alkylarylene groups, and wherein hetero atoms, such as oxygen, nitrogen, sulfur, silicon, phosphorus, boron, and the like either may or may not be present in either the aryl or the alkyl portion of the alkylarylene group), in one embodiment with at least about 6 carbon atoms, and in another embodiment with at least about 7 carbon atoms, and in one embodiment with no more than about 200 carbon atoms, in another embodiment with no more than about 100 carbon atoms, and in yet another embodiment with no more than about 50 carbon atoms, although the number of carbon atoms can be outside of these ranges, such as tolylene or the like, including (a) alkylarylene groups wherein both the alkyl and the aryl portions form the linkage between the —NR$_4$— groups, such as

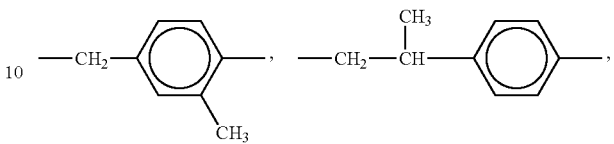

and the like, and (b) alkylarylene groups wherein only the aryl portion forms the linkage between the —NR$_4$— groups, such as

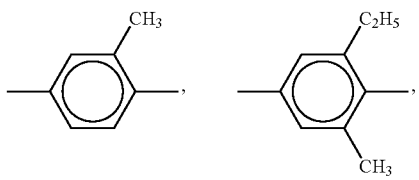

and the like, and R$_4$ is a hydrogen atom or an alkyl group (including linear, branched, saturated, unsaturated, substituted, and unsubstituted alkyl groups), in one embodiment with at least 1 carbon atom, and in one embodiment with no more than about 3 carbon atoms, although the number of carbon atoms can be outside of these ranges, wherein the substituents on the substituted alkyl, alkylene, aryl, arylene, arylalkyl, arylalkylene, alkylaryl, and alkylarylene groups in R$_1$, R$_2$, R$_3$, and R$_4$ can be (but are not limited to) halogen atoms, including fluorine, chlorine, bromine, and iodine atoms, imine groups, ammonium groups, cyano groups, pyridinium groups, ether groups, aldehyde groups, ketone groups, ester groups, carbonyl groups, thiocarbonyl groups, sulfide groups, sulfoxide groups, phosphine groups, nitrile groups, mercapto groups, nitro groups, nitroso groups, sulfone groups, acyl groups, urethane groups, urea groups, mixtures thereof, and the like, wherein two or more substituents can be joined together to form a ring.

Since hetero atoms can be included in the R$_1$ groups, R$_1$ also includes alkoxy, aryloxy, arylalkoxy, alkylaryloxy, polyalkyleneoxy, alkoxyalkyl, alkoxyaryl, pyrrolidine, imidazole, pyrimidinone, oxazoline, thiazoline, and like groups, provided that no oxygen atom is directly bonded to one of the —NH— groups. In addition, since hetero atoms can be included in the R$_1$ groups, R$_1$ also includes heterocyclic groups.

Since hetero atoms can be included in the R$_2$ groups, R$_2$ also includes alkyleneoxy, aryleneoxy, arylalkyleneoxy, alkylaryleneoxy, polyalkyleneoxy, alkoxyalkylene, alkoxyarylene, pyrrolidine, imidazole, pyrimidinone, oxazoline, thiazoline, and like groups, provided that no oxygen atom is directly bonded to one of the nitrogen atoms. In addition, since hetero atoms can be included in the R$_2$ groups, R$_2$ also includes heterocyclic groups.

Since hetero atoms can be included in the R$_3$ group, R$_3$ also includes alkyleneoxy, aryleneoxy, arylalkyleneoxy, alkylaryleneoxy, polyalkyleneoxy, alkoxyalkylene, alkoxyarylene, pyrrolidine, imidazole, pyrimidinone, oxazoline, thiazoline, and like groups, provided that no oxygen atom is directly bonded to one of the nitrogen atoms. In addition, since hetero atoms can be included in the $R_3$ group, $R_3$ also includes heterocyclic groups.

In one specific instance, $R_1$ has in one embodiment at least about 6 carbon atoms, in another embodiment at least about 8 carbon atoms, in yet another embodiment at least about 10 carbon atoms, in still another embodiment at least about 12 carbon atoms, in another embodiment at least about 14 carbon atoms, in yet another embodiment at least about 16 carbon atoms, and in still another embodiment at least about 18 carbon atoms, although the number of carbon atoms can be outside of these ranges.

In one specific instance, $R_1$ has in one embodiment no more than about 50 carbon atoms, in another embodiment no more than about 30 carbon atoms, and in yet another embodiment no more than about 18 carbon atoms, although the number of carbon atoms can be outside of these ranges.

In one specific instance, $R_2$ has in one embodiment at least about 3 carbon atoms, in another embodiment at least about 4 carbon atoms, in yet another embodiment at least about 5 carbon atoms, and in still another embodiment at least about 6 carbon atoms, although the number of carbon atoms can be outside of these ranges.

In one specific instance, $R_2$ has in one embodiment no more than about 50 carbon atoms, in another embodiment no more than about 36 carbon atoms, and in yet another embodiment no more than about 12 carbon atoms, although the number of carbon atoms can be outside of these ranges.

The bis(urea-urethane) compounds can be prepared as follows. A monoalcohol of the formula $R_1$—OH can be reacted with a diisocyanate of the formula OCN—$R_2$—NCO in approximately equimolar amounts at temperatures of from about room temperature to about 125° C., optionally in the presence of a catalyst, and in the presence of a solvent. Thereafter, the resulting product can be cooled to about room temperature and reacted with about 2 moles of product per every 1 mole of a diamine of the formula

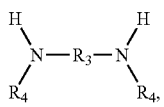

in the presence of a solvent, at temperatures of from about room temperature to about 125° C. The reaction proceeds as follows:

Mixtures of two or more reactants can also be employed to obtain varied products.

The monoalcohol and the diisocyanate are present in relative amounts of at least about 0.8 mole of monoalcohol per every one mole of diisocyanate, and of no more than about 1.2 moles of monoalcohol per every one mole of diisocyanate; in another embodiment the monoalcohol is present in an amount of no more than about 1 mole of monoalcohol per every one mole of diisocyanate.

Examples of suitable catalysts include (but are not limited to) Lewis acid catalysts such as dibutyl tin dilaurate, bismuth tris-neodecanoate, cobalt benzoate, lithium acetate, stannous octanoate, triethylamine, ferric chloride, aluminum trichloride, boron trichloride, boron trifluoride, titanium tetrachloride, tin tetrachloride, trialkylamines such as triethylamine, ethyldiisopropylamine, and 1,4-diazobicyclo(2.2.2)octane (DABCO™) and aromatic amines such as 4-(dimethylamino) pyridine, and the like. The catalyst, when present, is present in any desired or effective amount, in one embodiment at least about 0.1 mole percent (i.e., at least about 0.001 mole of catalyst per moles of monoalcohol), in another embodiment at least about 0.2 mole percent, in yet another embodiment at least about 0.5 mole percent, and in yet another embodiment at least about 1 mole percent, and in one embodiment no more than about 10 mole percent, in another embodiment no more than about 7.5 mole percent, and in yet another embodiment no more than about 5 mole percent, based on the amount of diisocyanate, although the amount can be outside of these ranges.

Examples of suitable solvents for the first part of the reaction include (but are not limited to) toluene, hexane, heptane, methylene chloride, tetrahydrofuran, diethyl ether, ethyl acetate, methyl ethyl ketone, and the like, as well as mixtures thereof. When present, the solvent is present in any desired amount, in one embodiment at least about 1 milliliter per millimole of diisocyanate, in another embodiment at least about 3 milliliters per millimole of diisocyanate, in yet another embodiment at least about 5 milliliters per millimole of diisocyanate, in still another embodiment at least about 7 milliliters per millimole of diisocyanate, in another embodiment at least about 8 milliliters per millimole of diisocyanate, in yet another embodiment at least about 10 milliliters per millimole of diisocyanate, in still another embodiment at least about 20 milliliters per millimole of diisocyanate, and in another embodiment at least about 30 milliliters per millimole of diisocyanate, and in one embodiment no more than about 50 milliliters per millimole of diisocyanate, in another

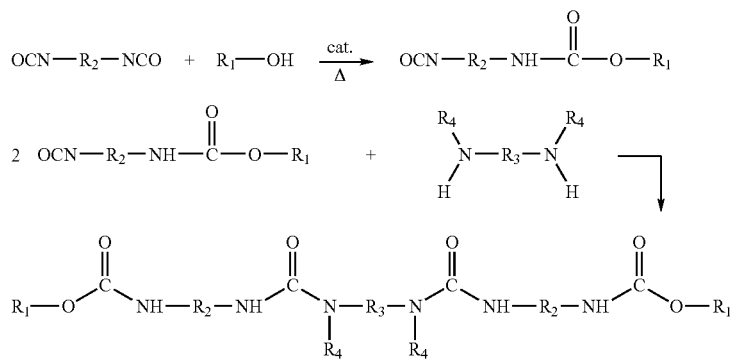

embodiment no more than about 30 milliliters per millimole of diisocyanate, in yet another embodiment no more than about 20 milliliters per millimole of diisocyanate, in still another embodiment no more than about 15 milliliters per millimole of diisocyanate, and in another embodiment no more than about 10 milliliters per millimole of diisocyanate, although the amount can be outside of these ranges.

The diisocyanate and the monoalcohol are heated to any desired or effective temperature, in one embodiment at least about 20° C., in another embodiment at least about 40° C., and in yet another embodiment at least about 50° C., and in one embodiment no more than about 125° C., in another embodiment no more than about 100° C., and in yet another embodiment no more than about 75° C., although the temperature can be outside of these ranges. In addition, the temperature can be varied within these or other ranges throughout the reaction.

The diisocyanate and the monoalcohol are reacted for any desired or effective period of time, in one embodiment at least about 5 minutes, in another embodiment at least about 10 minutes, and in yet another embodiment at least about 15 minutes, and in one embodiment no more than about 120 minutes, in another embodiment no more than about 90 minutes, and in yet another embodiment no more than about 60 minutes, although the time can be outside of these ranges.

Subsequent to the reaction between the diisocyanate and the monoalcohol, the first reaction product is not recovered; the reaction mixture can be cooled to room temperature and the diamine can be added to the reaction mixture, along with additional solvent if desired, to complete the reaction.

The first reaction product and the diamine are present in any desired or effective relative amounts, in one embodiment at least about 1.75 moles of first reaction product per every one mole of diamine, in another embodiment at least about 1.9 moles of first reaction product per every one mole of diamine, and in yet another embodiment at least about 2 moles of first reaction product per every one mole of diamine, and in one embodiment no more than about 2.3 moles of first reaction product per every one mole of diamine, in another embodiment no more than about 2.1 moles of first reaction product per every one mole of diamine, and in yet another embodiment no more than about 2 moles of first reaction product per every one mole of diamine, although the relative amounts can be outside of these ranges.

The first reaction product and the diamine are allowed to react at any desired or effective temperature, in one embodiment at least about 10° C., in another embodiment at least about 20° C., and in yet another embodiment at least about 30° C., and in one embodiment no more than about 75° C., in another embodiment no more than about 50° C., and in yet another embodiment no more than about 40° C., although the temperature can be outside of these ranges. In addition, the temperature can be varied within these or other ranges throughout the reaction.

The first reaction product and the diamine are allowed to react for any desired or effective period of time, in one embodiment at least about 5 minutes, in another embodiment at least about 10 minutes, and in yet another embodiment at least about 20 minutes, and in one embodiment no more than about 3 hours, in another embodiment no more than about 1.5 hours, and in yet another embodiment no more than about 1 hour, although the time can be outside of these ranges.

Thereafter, the product can be precipitated by addition of a small amount of a non-solvent, such as hexane, toluene, methyl ethyl ketone, methylene chloride, or the like, as well as mixtures thereof, followed by good stirring. The product can then be recovered by filtration.

The process disclosed herein enables the synthesis of the reaction product in desirably high yield and purity in a one-pot multireaction process with no need for isolation of intermediate products and no need for treatment of intermediate products. The process is thus highly desirable and efficient, does not result in the production of significant amounts of undesired byproducts, and does not require expensive and inefficient isolation and purification steps.

Specific embodiments will now be described in detail. These examples are intended to be illustrative, and the claims are not limited to the materials, conditions, or process parameters set forth in these embodiments. All parts and percentages are by weight unless otherwise indicated.

EXAMPLE I

Into a solution containing 1,6-diisocyanatohexane (27.7 mmol, 4.66 grams, obtained from Sigma-Aldrich Fine Chemicals, Milwaukee, Wis.) and hexane (250 milliliters) with stirring at room temperature was added a solution of 1-octadecanol (27.7 mmol, 7.5 grams; obtained from Sigma-Aldrich Fine Chemicals) in anhydrous tetrahydrofuran (50 milliliters, from Sigma-Aldrich Fine Chemicals) and dibutyl tin dilaurate (1 mol percent, 0.28 mmol, 0.18 gram; obtained from Sigma-Aldrich Fine Chemicals) as catalyst. The resulting solution was heated to 40° C. for 30 minutes and subsequently cooled to room temperature (20 to 25° C.). A solution of 3,3'-[(1,4-butanediol)bis(propylamine)] (NDPA-12, 2.83 grams, 13.9 mmol, obtained from Tomah Chemical, Milton, Wis.) in hexane (60 milliliters) was slowly added to the reaction mixture through an addition funnel. The mixture was stirred vigorously at room temperature for 30 minutes, during which a more viscous white precipitate was formed. IR spectroscopy indicated the presence of trace amounts of isocyanate. More 3,3'-[(1,4-butanediol) bis(propylamine)] (NDPA-12, 0.4 gram, 2 mol) was added and the mixture was stirred for an additional 30 minutes. IR spectroscopy indicated that all of the isocyanate was consumed. The product was isolated by vacuum filtration on a paper filter, rinsed with hexane, and dried under vacuum at 60° C. for 2 hours to give 14.33 grams of a white powder (93 percent yield). The product was believed to be of the formula

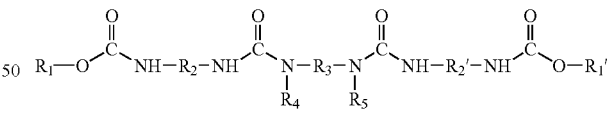

wherein $R_1$ and $R_1'$ were both —$(CH_2)_{17}CH_3$, $R_2$ and $R_2'$ were both —$(CH_2)_6$—, $R_3$ was —$(CH_2)_3$—O—$(CH_2)_4$—O—$(CH_2)_3$—, and $R_4$ and $R_5$ were both hydrogen atoms. $^1$H NMR analysis of the product indicated that the product was of high purity. $^1$H NMR (DMSO-$d_6$, at 100° C.); 0.91 ppm (multiplet, 3 H integration, C$\underline{H}_3$(CH$_2$)$_{16}$CH$_2$CONH—), 1.02-1.73 ppm (broad multiplet, 44 H integration, —CH$_3$(C$\underline{H}_2$)$_{16}$CH$_2$—, NHCONHCH$_2$(C$\underline{H}_2$)$_4$CH$_2$NHCO$_2$—, —CH$_2$C$\underline{H}_2$CH$_2$O—CH$_2$(C$\underline{H}_2$)$_2$CH$_2$—O—CH$_2$C$\underline{H}_2$CH$_2$—), 2.87-3.14 ppm (broad multiplets, 6 H integration, —O(CH$_2$)$_2$C$\underline{H}_2$NHCONHC$\underline{H}_2$(CH$_2$)$_4$C$\underline{H}_2$NHCO$_2$), 3.39 ppm (multiplet, 8 H, —(CH$_2$)$_2$C$\underline{H}_2$—O—C$\underline{H}_2$(CH$_2$)$_2$C$\underline{H}_2$—O—C$\underline{H}_2$(CH$_2$)$_2$—), 3.96 ppm (triplet, 2 H integration, CH$_3$(CH$_2$)$_{16}$CH$_2$—OCONH—), 5.53 ppm (broad singlet, 2 H integration, —NHCONH—), 6.49 ppm (broad singlet, 1 H integration —NHCO$_2$).

EXAMPLE II

Into a solution containing 1,6-diisocyanatohexane (3.50 grams, 20.8 mmol; obtained from Sigma-Aldrich Fine Chemicals) and hexane (250 milliliters) stirring at room temperature was added a solution of 1-octadecanol (5.63 grams, 20.8 mmol; obtained from Sigma-Aldrich Fine Chemicals) in anhydrous tetrahydrofuran (50 milliliters, obtained from Sigma-Aldrich Fine Chemicals) and dibutyl tin dilaurate (1 mol percent, 0.22 mmol, 0.14 gram; obtained from Sigma-Aldrich Fine Chemicals) as catalyst. The resulting solution was heated to 60° C. for 1 hour, during which a white precipitate was formed. The mixture was cooled to room temperature (20 to 25° C.). A solution of 1,12-diaminodecane (2.08 grams, 10.4 mmol; obtained from Sigma-Aldrich Fine Chemicals) in hexane (50 milliliters) was then slowly added to the reaction mixture. The mixture was stirred vigorously at room temperature for 1 hour, during which a more viscous white precipitate was formed. IR spectroscopy indicated the presence of trace amounts of isocyanate, which was quenched by adding methanol (5 milliliters). The product was isolated by vacuum filtration on a paper filter, rinsed with hexane, and dried under vacuum at 60° C. for 2 hours to give 8.18 grams of a white powder (73 percent yield). The product was believed to be of the formula

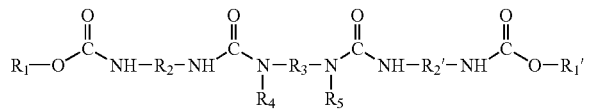

wherein R$_1$ and R$_1$' were both —(CH$_2$)$_{17}$CH$_3$, R$_2$ and R$_2$' were both —(CH$_2$)$_6$—, R$_3$ was —(CH$_2$)$_{12}$—, and R$_4$ and R$_5$ were both hydrogen atoms. The $^1$H NMR of this product was similar to that of Example I.

EXAMPLE III

Into a solution containing 1,6-diisocyanatohexane (4.33 grams, 25.7 mmol; obtained from Sigma-Aldrich Fine Chemicals) and hexane (250 milliliters) stirring at room temperature was added a solution of 1-docosanol (8.40 grams, 25.7 mmol; obtained from Sigma-Aldrich Fine Chemicals) in anhydrous tetrahydrofuran (50 milliliters, obtained from Sigma-Aldrich Fine Chemicals) and dibutyl tin dilaurate (1 mol percent, 0.25 mmol, 0.16 gram; obtained from Sigma-Aldrich Fine Chemicals) as catalyst. The resulting solution was heated to 60° C. for 1 hour, during which a white precipitate was formed. The mixture was cooled to room temperature (20 to 25° C.). A solution of 1,10-diaminodecane (2.21 grams, 12.9 mmol; obtained from Sigma-Aldrich Fine Chemicals) in hexane (50 milliliters) was then slowly added to the reaction mixture through an addition funnel. The mixture was stirred vigorously at room temperature for 1 hour, during which a more viscous white precipitate was formed. All of the isocyanate was consumed as indicated by IR spectroscopy. The product was isolated by vacuum filtration on a paper filter, rinsed with hexane, and dried under vacuum at 60° C. for 2 hours to give 13.8 grams of an off-white powder (93 percent yield). The product was obtained as a white powder in 93 percent yield. The product was believed to be of the formula

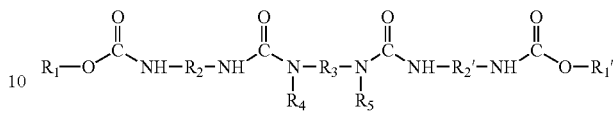

wherein R$_1$ and R$_1$' were both —(CH$_2$)$_{21}$CH$_3$, R$_2$ and R$_2$' were both —(CH$_2$)$_6$—, R$_3$ was —(CH$_2$)$_{10}$—, and R$_4$ and R$_5$ were both hydrogen atoms. The $^1$H NMR of this product was similar to that of Example I.

EXAMPLE IV

Into a solution containing 4,4'-methylene bis(cyclohexyl isocyanate) (4.2 grams, 16.01 mmol, obtained from Sigma-Aldrich Fine Chemicals) and hexane (250 milliliters) stirring at room temperature was added a solution of isostearyl alcohol (4.33 grams, 16.01 mmol; obtained from UniQema, Wilmington, Del.) in hexane (50 milliliters) and dibutyl tin dilaurate (1 mol percent, 0.16 mmol, 0.10 gram; obtained from Sigma-Aldrich Fine Chemicals) as catalyst. The resulting solution was heated to 50° C. for 1 hour, during which the solution turned cloudy. The reaction mixture was cooled to room temperature (20 to 25° C.). A solution of 3,3'-[(1,4-butanediol)bis(propylamine)] (NDPA-12, 1.63 grams, 8.01 mmol, obtained from Tomah Chemical, Milton, Wis.) in hexane (60 milliliters) was slowly added to the reaction mixture through an addition funnel. The mixture was stirred vigorously at room temperature for 1 hour, during which a viscous white precipitate was formed. IR spectroscopy indicated that all of the isocyanate was consumed. The product was isolated by vacuum filtration on a paper filter, rinsed with hexane, and dried under vacuum at 40° C. for 30 minutes to give 7.3 grams of a white powder (72 percent yield). The product was believed to be of the formula

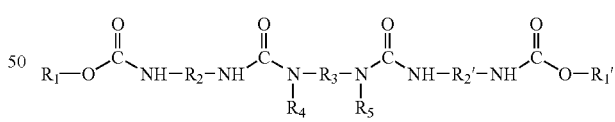

wherein R$_1$ and R$_1$' were both

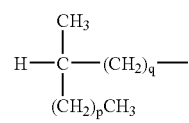

wherein q is an integer of from about 10 to about 15, p is an integer of from 0 to about 3, and the sum of p+q=15, R$_2$ and R$_2$' were both

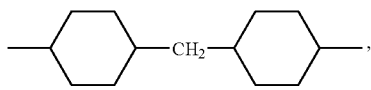

$R_3$ was —$(CH_2)_3$—O—$(CH_2)_4$—O—$(CH_2)_3$—, and $R_4$ and $R_5$ were both hydrogen atoms.

EXAMPLE V

Into a solution containing 1,6-diisocyanatohexane (5.55 grams, 33.0 mmol; available from Sigma-Aldrich Fine Chemicals) and methyl ethyl ketone (250 milliliters, available from Sigma-Aldrich Fine Chemicals) stirring at room temperature is added a solution of 1-dodecanol (6.15 grams, 33.0 mmol; available from Sigma-Aldrich Fine Chemicals) in methyl ethyl ketone (50 milliliters) and 4-(dimethylamino) pyridine (3.27 mmol, 0.40 gram; available from Sigma-Aldrich Fine Chemicals) as catalyst. The resulting solution is heated to 60° C. for 1 hour, during which it is believed that a white precipitate will form. The mixture is then cooled to room temperature (20 to 25° C.). A solution of 4,4'-methylene bis(phenyl amine) (3.30 gram, 16.5 mmol; available from Sigma-Aldrich Fine Chemicals) in methyl ethyl ketone (50 milliliters) is then slowly added to the reaction mixture through an addition funnel. The mixture is stirred vigorously at room temperature for 1 hour, during which it is believed that a more viscous white precipitate will be formed. The product can be isolated by vacuum filtration on a paper filter, rinsed with hexane, and dried under vacuum at 60° C. for 2 hours. It is believed that the product will be of the formula

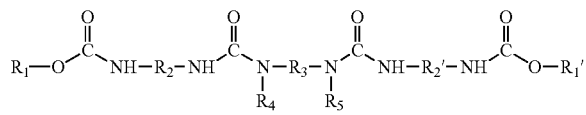

wherein $R_1$ and $R_1'$ are both —$(CH_2)_{11}CH_3$, $R_2$ and $R_2'$ are both —$(CH_2)_6$—, $R_3$ is

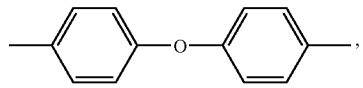

and $R_4$ and $R_5$ are both hydrogen atoms.

EXAMPLE VI

Into a 500 milliliter round bottom flask is added a solution of 1-octadecanol (27.7 mmol, 7.5 grams; available from Aldrich Chemical Co.) in dry tetrahydrofuran (50 milliliters). Thereafter, hexane (250 milliliters) is added to this solution, followed by a solution of 4,4'-methylene bis(phenyl isocyanate) (27.8 mmol, 6.96 grams, available from Aldrich Chemical Co.) in hexane (50 milliliters) and dibutyl tin dilaurate (1 mol percent, 0.28 mmol, 0.18 gram, available from Sigma-Aldrich Fine Chemicals) as catalyst. The resulting solution is heated to 40° C. for 30 minutes and subsequently cooled to room temperature (20 to 25° C.). A solution of 3,3'-[(1,4-butanediol)bis(propylamine)] (NDPA-12, 2.57 grams, 12.6 mmol, available from Tomah Chemical) in hexane (60 milliliters) is slowly added to the reaction mixture through an addition funnel. The mixture is stirred vigorously at room temperature for 30 minutes, during which it is believed that a more viscous white precipitate will be formed. The product is isolated by vacuum filtration on a paper filter, rinsed with hexane, and dried under vacuum at 60° C. for 2 hours. It is believed that a compound of the formula

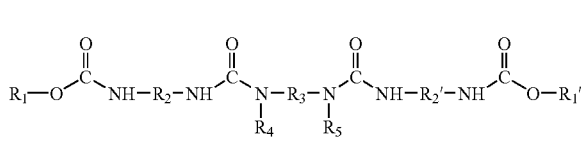

wherein $R_1$ and $R_1'$ are both —$(CH_2)_{17}CH_3$, $R_2$ and $R_2'$ are both

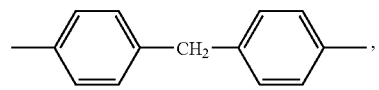

$R_3$ is —$(CH_2)_3$—O—$(CH_2)_4$—O—$(CH_2)_3$—, and $R_4$ and $R_5$ are both hydrogen atoms will be obtained.

EXAMPLE VII

Into a solution containing 1,6-diisocyanatohexane (27.8 mmol, 4.66 grams, available from Sigma-Aldrich Fine Chemicals) and hexane (250 milliliters) stirring at room temperature is added a solution of 4-phenyl phenol (27.8 mmol, 4.73 grams; available from Sigma-Aldrich Fine Chemicals) in anhydrous tetrahydrofuran (50 milliliters; available from Sigma-Aldrich Fine Chemicals) and dibutyl tin dilaurate (1 mol percent, 0.16 gram; available from Sigma-Aldrich Fine Chemicals) as catalyst. The resulting solution is heated to 40° C. for 30 minutes and subsequently cooled to room temperature (20 to 25° C.). A solution of 3,3'-[(1,4-butanediol)bis (propylamine)] (NDPA-12, 2.57 grams, 12.6 mmol; available from Tomah Chemical, Milton, Wis.) in hexane (60 milliliters) is slowly added to the reaction mixture through an addition funnel. The mixture is stirred vigorously at room temperature for 30 minutes, during which it is believed that a more viscous white precipitate will form. The product can be isolated by vacuum filtration on a paper filter, rinsed with hexane, and dried under vacuum at 60° C. for 2 hours. It is believed that a compound of the formula

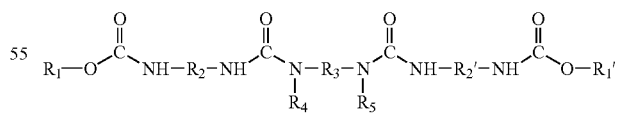

wherein $R_1$ and $R_1'$ are both

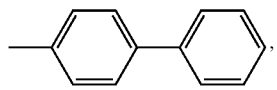

$R_2$ and $R_2{'}$ are both —$(CH_2)_6$—, $R_3$ is —$(CH_2)_3$—O—$(CH_2)_4$—O—$(CH_2)_3$—, and $R_4$ and $R_5$ are both hydrogen atoms will be obtained.

EXAMPLE VIII

Into a solution containing 1,6-diisocyanatohexane (2.35 grams, 14 mmol; obtained from Sigma-Aldrich Fine Chemicals) and hexane (75 milliliters, obtained from Sigma-Aldrich Fine Chemicals) stirring at room temperature was added 1,4-butanediol vinyl ether (1.62 grams, 14 mmol, obtained from Sigma-Aldrich Fine Chemicals) and dibutyltin dilaurate (0.088 grams, 0.14 mmol, obtained from Sigma-Aldrich Fine Chemicals) as the catalyst. The mixture was stirred and heated to an internal temperature of about 45° C. for 25 minutes. The progress of the reaction was monitored by $^1$H-NMR spectroscopy for consumption of the 1,4-butanediol vinyl ether reactant, indicated by the disappearance of the —$CH_2OH$ multiplet, which appears at 3.5 ppm as a shoulder peak on the downfield end of the intermediate isocyanate product whose signal is located at 3.35-3.40 ppm. The mixture was cooled to about 15° C. internal temperature, after which to this mixture was added dropwise a solution of 1,8-diaminooctane (1.2 grams, 8.3 mmol; obtained from Sigma-Aldrich Fine Chemicals) dissolved in anhydrous tetrahydrofuran (10 milliliters). The mixture was stirred for about 60 minutes while warming up to room temperature, and thickened to form a gelatinous slurry. FTIR spectroscopic analysis of a reaction sample showed little unreacted isocyanate (peak at 2180 cm$^{-1}$, sample prepared as a KBr pellet). Any residual isocyanate was quenched by addition of methanol (5 milliliters). The reaction mixture was then filtered by vacuum filtration to give a semi-solid product, which was subsequently stirred in hexane to ensure full precipitation. The solid product was filtered and dried in air to give 4.59 grams of a white powder (92 percent yield). The product was believed to be of the formula

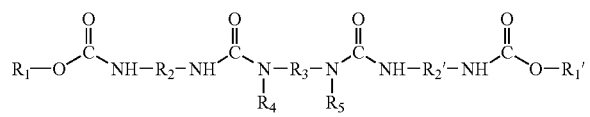

wherein $R_1$ and $R_1{'}$ were both

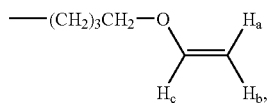

$R_2$ and $R_2{'}$ were both —$(CH_2)_6$—, $R_3$ was —$(CH_2)_8$—, and $R_4$ and $R_5$ were both hydrogen atoms. $^1$H-NMR spectroscopic analysis of the solid was performed in DMSO-$d_6$ (300 mHz) at high temperature (100° C.) and indicated the above structure with the following assigned peaks: 1.27-1.80 ppm (several multiplets, 34 H integration, methylene protons); 2.65 ppm (multiplet, 2 H integration, —NH(C═O)NH$CH_2$($CH_2$)$_6$$CH_2$NH(C═O)NH—); 2.95 ppm (multiplet, 8 H integration, —O(C═O)NH$CH_2$($CH_2$)$_4$$CH_2$NH(C═O)NH—); 3.80 ppm (multiplet, 4 H integration, —NH(C═O)O$CH_2CH_2CH_2$$CH_2$—O—C($H_c$)═C($H_a$)($H_b$)); 4.0 ppm (multiplet, 6 H integration, —NH(C═O)O$CH_2CH_2CH_2CH_2$—O—C($H_c$)═C($H_a$)($H_b$)); 4.25 ppm (doublet, 2 H integration, —O—C($H_c$)═C($H_a$)($H_b$); 5.50 ppm and 5.70 ppm (broad singlets, each 2 H integration, urea NH protons); 6.45 ppm (doublet of doublets, 2 H integration, —O—C($H_c$)═C($H_a$)($H_b$)); 6.60 ppm (broad singlet, 2 H integration, urethane NH proton). Elemental analysis calculated for C: 60.64%, H: 9.53%, N: 11.78%; found for C: 59.67%, H: 9.11%, N: 12.17%.

EXAMPLE IX

Into a solution containing 1,6-diisocyanatohexane (4.04 grams, 24.0 mmol; obtained from Sigma-Aldrich Fine Chemicals, Milwaukee, Wis.) and anhydrous tetrahydrofuran (100 mL, Sigma-Aldrich Fine Chemicals, Milwaukee, Wis.) stirring at room temperature was added 2-ethylhexanol (3.13 grams, 24.0 mmol, obtained from Sigma-Aldrich Fine Chemicals) and dibutyltin dilaurate (0.38 grams, 0.6 mmol, obtained from Sigma-Aldrich Fine Chemicals) as the catalyst. The mixture was stirred and heated to an internal temperature of about 70° C. The progress of the reaction was monitored by $^1$H-NMR spectroscopy for the consumption of 2-ethylhexanol starting material, indicated by the disappearance of the —$CH_2OH$ multiplet, which appears at 3.5 ppm as a shoulder peak on the downfield end of the intermediate isocyanate product whose signal is located at 3.35-3.40 ppm. The mixture was cooled to about 5° C. internal temperature; thereafter, to this mixture was added dropwise a solution of trans-1,2-diaminocyclohexane (1.37 grams, 12 mmol; obtained as a racemic mixture of (1R,2R) and (1S,2S) stereoisomers from Sigma-Aldrich Fine Chemicals) dissolved in anhydrous tetrahydrofuran (10 mL). The mixture was stirred for about 30 minutes while warming up to room temperature, and thickened to form a gelatinous slurry. FTIR spectroscopic analysis of a reaction sample showed very little unreacted isocyanate (peak at 2180 cm$^{-1}$, sample prepared as a KBr pellet). Residual isocyanate was quenched by addition of 5 mL of methanol. A crystalline product was isolated from the slurry by first adding methylene chloride (40 mL) followed with stirring for approximately 20 minutes to ensure full precipitation out of the gel slurry. The solid was filtered by suction on a paper filter, rinsed with methylene chloride (about 10 mL), and then dried in air to give 7.36 grams of off-white solid (86% yield). The product was believed to be of the formulae

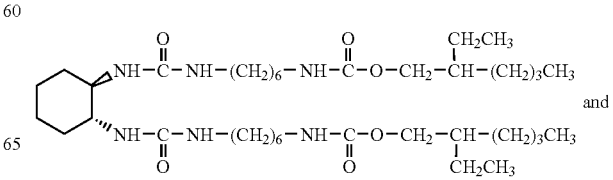

-continued

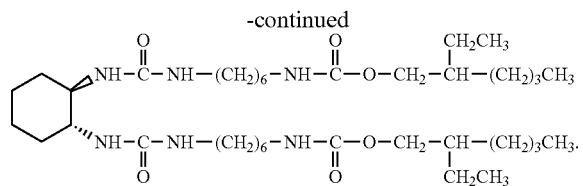

$^1$H-NMR spectroscopic analysis of the solid was performed in DMSO-$d_6$ (300 MHz) at high temperature (60° C.) and indicated the above structure, with the following assigned peaks: 0.90 ppm (multiplet, 6 H integration, —OCH$_2$CH(CH$_2$CH$_3$)CH$_2$CH$_2$CH$_3$); 1.0-1.95 ppm (broad multiplets, 20 H integration, 8 methylene protons from 2-ethylhexanol portion, 8 methylene protons from the 1,6-diisocyanatohexane portion, and 4 methylene protons from the cyclohexane ring portion); 2.95 ppm (narrow multiplet, 4 H integration, —NH(C═O)NHCH$_2$(CH$_2$)$_4$CH$_2$NH(C═O)O); 3.20 ppm (broad singlet, 1 H integration, tertiary methine proton adjacent to urea group on cyclohexane ring); 3.90 ppm (doublet, 2 H integration, OCH$_2$CH(CH$_2$CH$_3$)CH$_2$CH$_2$CH$_3$); 5.65 ppm and 5.75 ppm (each a broad singlet, 1 H integration, urea NH protons); 6.75 ppm (broad singlet, 1 H integration, urethane NH proton). Elemental analysis calculated for C: 64.19%, H: 10.49%, N: 11.82%; found for C: 61.70%, H: 9.86%, N: 14.91%.

EXAMPLE X

Into a solution containing 1,6-diisocyanatohexane (4.04 grams, 24.0 mmol; obtained from Sigma-Aldrich Fine Chemicals) and anhydrous tetrahydrofuran (100 mL, obtained from Sigma-Aldrich Fine Chemicals) stirring at room temperature was added 1-octanol (3.13 grams, 24.0 mmol, obtained from Sigma-Aldrich Fine Chemicals) and dibutyltin dilaurate (0.15 grams, 0.24 mmol, obtained from Sigma-Aldrich Fine Chemicals) as the catalyst. The mixture was stirred and heated to an internal temperature of about 65° C. The progress of the reaction was monitored by $^1$H-NMR spectroscopy for the consumption of 1-octanol starting material, indicated by the disappearance of the —CH$_2$OH multiplet, which appears at 3.6 ppm downfield of the intermediate isocyanate product whose signal is located at 3.35 ppm. The mixture was cooled to about 15° C. internal temperature; thereafter, to this mixture was added dropwise a solution of trans-1,2-diaminocyclohexane (1.37 grams, 12 mmol; obtained as a racemic mixture of (1R,2R) and (1S,2S) stereoisomers from Sigma-Aldrich Fine Chemicals) dissolved in anhydrous tetrahydrofuran (10 mL). The mixture was stirred for about 60 minutes while warming up to room temperature, and thickened to form a gelatinous slurry. FTIR spectroscopic analysis of a reaction sample showed very little unreacted isocyanate (peak at 2180 cm$^{-1}$, sample prepared as a KBr pellet). Residual isocyanate was quenched by addition of 5 mL of methanol. A crystalline product was isolated from the slurry by first adding diethyl ether (20 mL) followed with stirring for approximately 30 minutes to ensure full precipitation out of the gel slurry. The solid was filtered by suction on a paper filter, rinsed with diethyl ether, and then dried in air to give 6.20 grams of off-white solid (77.5% yield). The product was believed to be of the formulae

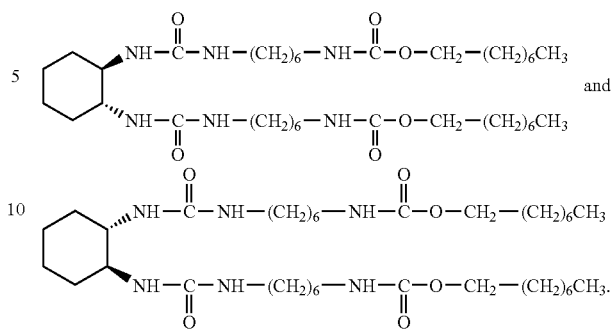

$^1$H-NMR spectroscopic analysis of the solid was performed in DMSO-$d_6$ (300 MHz) at high temperature (60° C.) and indicated the above structure with the following assigned peaks: 0.90 ppm (multiplet, 3 H integration, —OCH$_2$(CH$_2$)$_6$CH$_3$); 1.05-1.95 ppm (broad multiplets, 24 H integration, 12 methylene protons from 2-ethylhexanol portion, 8 methylene protons from the 1,6-diisocyanatohexane portion, and 4 methylene protons from the cyclohexane ring portion); 2.95 ppm (narrow multiplet, 4 H integration, —NH(C═O)NH CH$_2$(CH$_2$)$_4$CH$_2$NH(C═O)O); 3.35 ppm (doublet, 1 H integration, tertiary methine proton adjacent to urea group on cyclohexane ring); 3.90 ppm (doublet of doublets, 2 H integration, NH(C═O)OCH$_2$(CH$_2$)$_6$CH$_3$; 5.70 ppm and 5.85 ppm (each a broad singlet, 1 H integration, urea NH protons); 7.00 ppm (broad singlet, 1 H integration, urethane NH proton). Elemental analysis calculated for C: 64.19%, H: 10.49%, N: 11.82%; found for C: 64.46%, H: 10.63%, N: 10.69%.

EXAMPLE XI

Into a solution containing 1,6-diisocyanatohexane (2.35 grams, 13.95 mmol; obtained from Sigma-Aldrich Fine Chemicals) and anhydrous hexane (100 mL, obtained from Sigma-Aldrich Fine Chemicals) stirring at room temperature was added diethylene glycol butyl ether (2.27 grams, 14.0 mmol, obtained from Sigma-Aldrich Fine Chemicals), which was previously dried over calcium chloride granules, and dibutyltin dilaurate as catalyst (0.095 grams, 0.15 mmol, obtained from Sigma-Aldrich Fine Chemicals). The mixture was stirred and heated to an internal temperature of about 45° C. The progress of the reaction was monitored by $^1$H-NMR spectroscopy for the consumption of the diethylene glycol butyl ether starting material. The mixture was cooled to about 15° C. internal temperature; thereafter, to this mixture was added dropwise a solution of trans-1,2-diaminocyclohexane (0.80 grams, 7.0 mmol; obtained as a racemic mixture of (1R,2R) and (1S,2S) stereoisomers from Sigma-Aldrich Fine Chemicals) dissolved in anhydrous hexane (20 mL). The mixture was stirred for about 30 minutes while warming up to room temperature, and FTIR spectroscopic analysis of a reaction sample indicated no unreacted isocyanate (peak at 2180 cm$^{-1}$, sample prepared as a KBr pellet). The crystalline product was isolated by vacuum filtration on filter paper, rinsed with hexane, and then dried in air to give 4.82 grams of a white powder (88.8% yield). The product was believed to be of the formulae

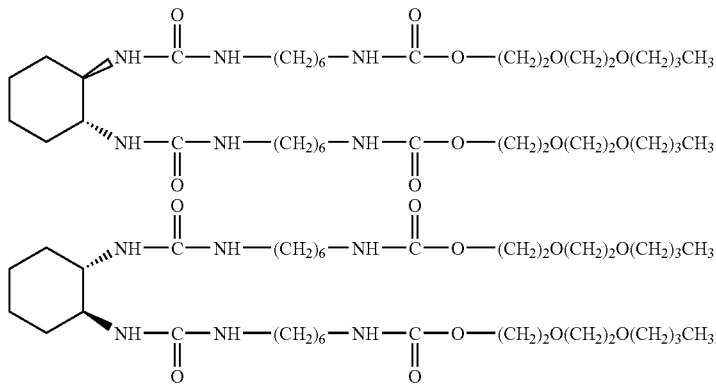

$^1$H-NMR spectroscopic analysis of the solid was performed in DMSO-$d_6$ (300 MHz) at 80° C. and indicated the above structure with the following assigned peaks: 0.90 ppm (multiplet, 3 H integration, —OCH$_2$CH$_2$OCH$_2$CH$_2$OCH$_2$CH$_2$CH$_2$C$\underline{H}_3$); 1.05-1.95 ppm (broad multiplets, 16 H integration, 4 methylene protons from butyl ether terminus, 8 methylene protons from the 1,6-diisocyanatohexane portion, and 4 methylene protons from the cyclohexane ring portion); 3.0 ppm (narrow multiplet, 5 H integration, —NH(C=O)NHC$\underline{H}_2$(CH$_2$)$_4$C$\underline{H}_2$NH(C=O)O and also tertiary methine proton adjacent to urea group on cyclohexane ring); 3.40-3.70 ppm (multiplets, 8 H integration, NH(C=O)OCH$_2$C$\underline{H}_2$OC$\underline{H}_2$C$\underline{H}_2$OC$\underline{H}_2$CH$_2$CH$_2$CH$_3$); 4.10 ppm (singlet, 2 H integration, NH(C=O)OC$\underline{H}_2$CH$_2$OCH$_2$CH$_2$OCH$_2$CH$_2$CH$_2$CH$_3$); 5.60 ppm and 5.70 ppm (each a broad singlet, 1 H integration, urea NH protons); 6.75 ppm (broad singlet, 1 H integration, urethane NH proton). Elemental analysis calculated for C: 58.83%, H: 9.54%, N: 10.83%; found for C: 58.81%, H: 9.58%, N: 12.17%.

EXAMPLE XII

Into a solution containing 1,6-diisocyanatohexane (1.86 grams, 11.09 mmol; obtained from Aldrich Fine Chemicals) and hexane (250 milliliters) stirring at room temperature was added a solution of 1-octadecanol (3.0 grams, 11.09 mmol; obtained from Aldrich Fine Chemicals) in anhydrous tetrahydrofuran (50 milliliters, obtained from Aldrich Fine Chemicals) and dibutyl tin dilaurate (0.07 gram, 1 mol %; obtained from Aldrich Fine Chemicals) as catalyst. The resulting solution was heated to 60° C. for 1 hour, during which a white precipitate was formed. The mixture was cooled to room temperature (20 to 25° C.). A solution of trans-1,2-diaminocyclohexane (0.69 gram, 6.09 mmol; obtained from Aldrich Fine Chemicals) in hexane (50 milliliters) was then slowly added to the reaction mixture through an addition funnel. The mixture was stirred vigorously at room temperature for 2 hours, during which a more viscous white precipitate was formed. An IR spectrum indicated the presence of trace amounts of isocyanate. More trans-1,2-diaminocyclohexane was added (0.1 gram, 0.87 mmol) and stirred for an additional 30 minutes, during which all of the isocyanate was consumed as shown by IR. The product was isolated by vacuum filtration on a paper filter, rinsed with hexane, and dried under vacuum at 60° C. for 2 hours to give 5 grams of an off-white powder (91 percent yield). The product was believed to be of the formulae

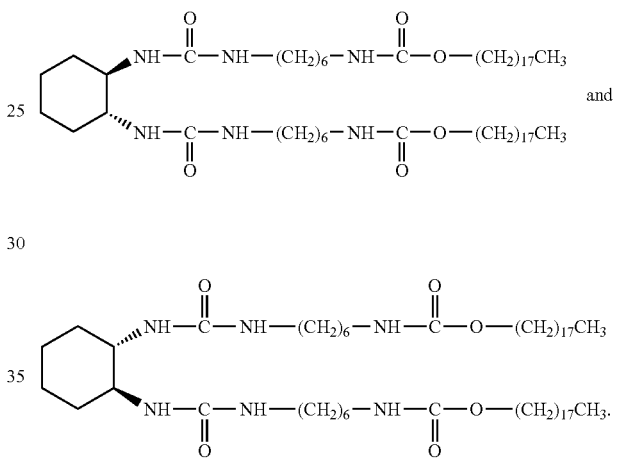

IR and $^1$H NMR analysis of the product indicated that product was of high purity. IR (KBr) 3318, 2921, 2849, 1684, 1634, 1539, 1276 cm$^{-1}$; $^1$H NMR (DMSO-$d_6$, at 100° C.); 0.89 ppm (triplet, 6 H integration, C$\underline{H}_3$(CH$_2$)$_{16}$CH$_2$CONH—), 1.01-1.82 ppm (multiplet, 86 H, 6 methylene protons on cyclohexyl ring, —NHCONHCH$_2$(C$\underline{H}_2$)$_4$CH$_2$NHCO$_2$—, CH$_3$(C$\underline{H}_2$)$_{16}$CH$_2$CONH—), 1.83 ppm (broad doublet, 0.4 H, CH on the cyclohexyl rings adjacent to carbons bonded to the NH urea), 1.89 ppm (broad doublet, 1.6 H, tertiary methine proton adjacent to urea group on cyclohexane ring), 2.25 ppm (doublet of triplet, 0.2 H —NHCONHC$\underline{H}_2$(CH$_2$)$_4$C$\underline{H}_2$NHCO$_2$—), 2.8 ppm (doublet of doublets, 0.3 H, CH on cyclohexyl ring next to NH urea), 3.00 ppm (quartet, 7.8 H, —NHCONHC$\underline{H}_2$(CH$_2$)$_4$C$\underline{H}_2$NHCO$_2$—), 3.18 ppm (multiplet, 1.7 H, CH on cyclohexyl ring next to NH urea), 4.02 ppm (triplet, 4 H, —NHCO$_2$C$\underline{H}_2$(CH$_2$)$_{16}$CH$_3$), 5.37 (broad triplet, 0.7 H, —N$\underline{H}$CON$\underline{H}$—), 5.71 ppm (broad doublet, 3.3 H, —N$\underline{H}$CON$\underline{H}$—), 6.48 ppm (broad singlet, 2 H, —N$\underline{H}$CO$_2$—), melting point by DSC 119.5° C.

EXAMPLE XIII

Into a solution containing 1,6-diisocyanatohexane (2.07 grams, 12.34 mmol; obtained from Sigma-Aldrich Fine Chemicals) and hexane (250 milliliters) with stirring at room temperature was added a solution of 1-dodecanol (2.30 grams, 12.34 mmol; obtained from Sigma-Aldrich Fine Chemicals) in anhydrous tetrahydrofuran (50 milliliters, obtained from Aldrich Fine Chemicals) and dibutyl tin dilaurate (0.08 gram, 1 mol %; obtained from Sigma-Aldrich Chemical Company) as catalyst. The resulting solution was heated to 45° C. for 1 hour, during which a white precipitate was formed. The mixture was cooled to room temperature (20 to 25° C.). A solution of trans-1,2-diaminocyclohexane (0.775 gram, 6.79 mmol; obtained as a racemic mixture of (1R,2R) and (1S,2S) stereoisomers from Sigma-Aldrich Fine Chemicals) in hexane (50 milliliters) was then slowly added to the reaction mixture through an addition funnel. The mixture was stirred at room temperature for 1 hour, during which a more viscous white precipitate was formed. An IR spectrum indicated the presence of trace amount of isocyanate. More trans-1,2-diaminocyclohexane was added (0.07 gram, 0.6 mmol) and stirred for an additional 30 minutes, during which all the isocyanate was consumed as shown by IR. The product was isolated by vacuum filtration on a paper filter, rinsed with hexane, and dried under vacuum at 60° C. for 2 hours to give 4.6 grams of product as an off-white powder (90 percent yield). The product was believed to be of the formulae

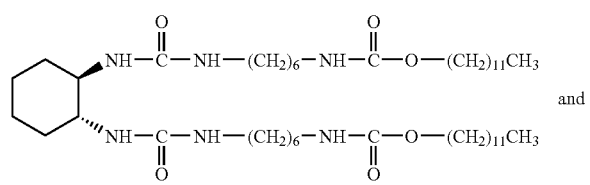

and

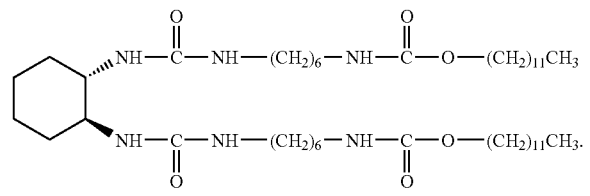

$^1$H NMR analysis of the product indicated that product was of high purity. IR (KBr) 3320, 2919, 2851, 1684, 1635, 1538, 1265 cm$^{-1}$; $^1$H NMR (DMSO-d$_6$, at 80° C.); 0.89 ppm (triplet, 6 H, CH$_3$(CH$_2$)$_{16}$CH$_2$CONH—), 1.01-1.80 ppm (multiplet, 62 H, 6 methylene protons on cyclohexyl ring, —NH-CONHCH$_2$(CH$_2$)$_4$CH$_2$NHCO$_2$—, CH$_3$(CH$_2$)$_{16}$CH$_2$CONH—), 1.87 ppm (broad doublet, 2 H, one of the CH$_2$ hydrogens on the cyclohexyl ring adjacent to carbons bonded to the NH urea), 2.98 ppm (quartet, 8 H, —NH-CONHCH$_2$(CH$_2$)$_4$CH$_2$NHCO$_2$—), 3.24 ppm (multiplet, 2 H, CH on cyclohexyl ring next to NH urea), 4.93 ppm (triplet, 4 H, —NHCO$_2$CH$_2$(CH$_2$)$_{16}$CH$_3$), 5.56 ppm (broad singlet, 2 H, —NHCONH—), 5.60 ppm (broad multiplet, 2 H, —NHCONH—), 6.60 ppm (broad singlet, 2 H, —NHCO$_2$—), melting point by DSC 111.7° C.

EXAMPLE XIV

The process of Example IX is repeated except that 4-phenylphenol is used instead of 2-ethylhexanol. A solution of 4-phenylphenol (4.08 grams, 24.0 mmol; available from Sigma-Aldrich Fine Chemicals, Milwaukee, Wis.) dissolved in anhydrous tetrahydrofuran (100 mL, available from Sigma-Aldrich Fine Chemicals) is added into a second solution containing 1,6-diisocyanatohexane (4.04 grams, 24.0 mmol; available from Sigma-Aldrich Fine Chemicals) dissolved in anhydrous tetrahydrofuran (100 mL) stirring at room temperature. Dibutyltin dilaurate (0.38 grams, 0.6 mmol, available from Sigma-Aldrich Fine Chemicals) is added as the catalyst, and the mixture is heated to an internal temperature of about 80° C. for 30 to 60 minutes. The mixture is then cooled to about 20° C. internal temperature, after which is then added dropwise to the mixture a solution of trans-1,2-diaminocyclohexane (1.37 grams, 12 mmol; available as a racemic mixture of (1R,2R) and (1S,2S) stereoisomers from Sigma-Aldrich Fine Chemicals) dissolved in anhydrous tetrahydrofuran (10 mL). The mixture is stirred for about 60 minutes while warming up to room temperature. Residual isocyanate is quenched by addition of 5 mL of methanol. It is believed that a crystalline product can be precipitated from the mixture by the addition of hexane (40 mL) followed with stirring for approximately 30 minutes. The solid can be recovered by vacuum filtration, rinsed with hexane and diethyl ether (about 10 mL each), and then dried in air. It is believed that compounds of the formulae

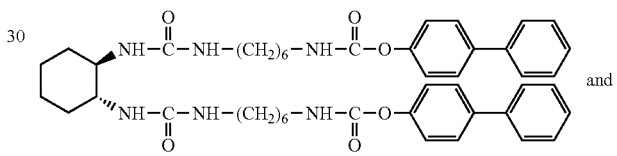

and

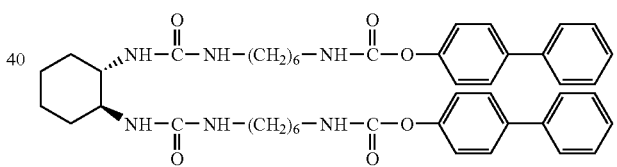

will be obtained.

EXAMPLE XV

The process of Example XIV is repeated except that 3-pentadecylphenol is used in place of 4-phenylphenol. A solution of 3-pentadecylphenol (7.31 grams, 24.0 mmol; available from Sigma-Aldrich Fine Chemicals) dissolved in anhydrous tetrahydrofuran (100 mL, available from Sigma-Aldrich Fine Chemicals) is added into a second solution containing 1,6-diisocyanatohexane (4.04 grams, 24.0 mmol; available from Sigma-Aldrich Fine Chemicals) dissolved in anhydrous tetrahydrofuran (100 mL) stirring at room temperature. Dibutyltin dilaurate (0.38 grams, 0.6 mmol, available from Sigma-Aldrich Fine Chemicals) is added as the catalyst, and the mixture is heated to an internal temperature of about 80° C. for 30 to 60 minutes. The mixture is then cooled to about 20° C. internal temperature, after which is added dropwise to the mixture a solution of trans-1,2-diaminocyclohexane (1.37 grams, 12 mmol; available as a racemic mixture of (1R,2R)

and (1S,2S) stereoisomers from Sigma-Aldrich Fine Chemicals) dissolved in anhydrous tetrahydrofuran (10 mL). The mixture is stirred for about 60 minutes while warming up to room temperature. Residual isocyanate is quenched by addition of 5 mL of methanol. It is believed that a crystalline product can be precipitated from the mixture by the addition of hexane (40 mL) followed with stirring for approximately 30 minutes. The solid can be recovered by vacuum filtration, rinsed with hexane and diethyl ether (about 10 mL each), and then dried in air. It is believed that compounds of the formulae

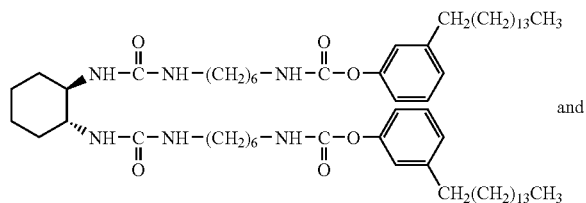

and

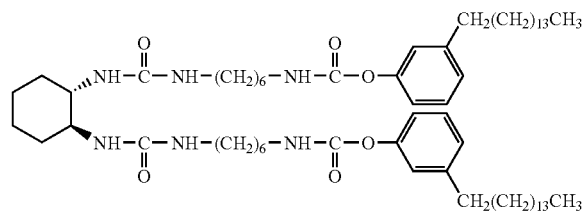

will be obtained.

EXAMPLE XVI

The process of Example XIV is repeated except that 4-phenyl-1-butanol is used in place of 4-phenylphenol. A solution of 4-phenyl-1-butanol (3.60 grams, 24.0 mmol; available from Sigma-Aldrich Fine Chemicals) dissolved in anhydrous tetrahydrofuran (100 mL, available from Sigma-Aldrich Fine Chemicals) is added into a second solution containing 1,12-diisocyanatododecane (6.06 grams, 24.0 mmol; available from Sigma-Aldrich Fine Chemicals) dissolved in anhydrous tetrahydrofuran (100 mL) stirring at room temperature. Dibutyltin dilaurate (0.38 grams, 0.6 mmol, available from Sigma-Aldrich Fine Chemicals) is added as the catalyst, and the mixture is heated to an internal temperature of about 80° C. for 30 to 60 minutes. The mixture is then cooled to about 20° C. internal temperature, after which is added dropwise to the mixture a solution of trans-1,2-diaminocyclohexane (1.37 grams, 12 mmol; available as a racemic mixture of (1R,2R) and (1S,2S) stereoisomers from Sigma-Aldrich Fine Chemicals) dissolved in anhydrous tetrahydrofuran (10 mL). The mixture is stirred for about 60 minutes while warming up to room temperature. Residual isocyanate is quenched by addition of 5 mL of methanol. It is believed that a crystalline product can be precipitated from the mixture by the addition of hexane (40 mL) followed with stirring for approximately 30 minutes. The solid can be recovered by vacuum filtration, rinsed with hexane and diethyl ether (about 10 mL each), and then dried in air. It is believed that compounds of the formulae

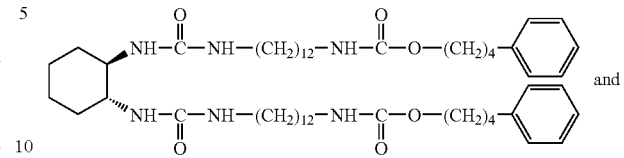

and

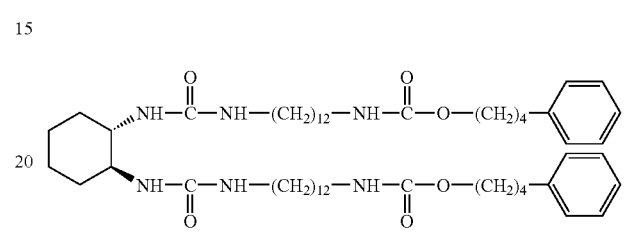

will be obtained.

EXAMPLE XVII

To a solution containing 1,6-diisocyanatohexane (5.04 grams, 30 mmol; obtained from Sigma-Aldrich Fine Chemicals, Milwaukee, Wis.) and anhydrous tetrahydrofuran (100 milliliters) stirring at room temperature was added 1,4-butanediol vinyl ether (3.48 grams, 30 mmol; obtained from Sigma-Aldrich Fine Chemicals) and dibutyltin dilaurate (0.19 grams, 0.3 mmol; obtained from Sigma-Aldrich Fine Chemicals) as the catalyst. The mixture was stirred and heated to an internal temperature of about 65° C. for 25 minutes. The progress of the reaction was monitored by $^1$H-NMR spectroscopy for consumption of the 1,4-butanediol vinyl ether reactant, indicated by the disappearance of the —CH$_2$OH multiplet, which appears at 3.5 ppm as a shoulder peak on the downfield end of the intermediate isocyanate product whose signal is located at 3.35-3.40 ppm. The mixture was cooled to about 15° C. internal temperature after which to this mixture was added dropwise a solution of trans-1,2-diaminocyclohexane (1.71 grams, 15 mmol; obtained as a racemic mixture of (1R,2R) and (1S,2S) stereoisomers from Sigma-Aldrich Fine Chemicals) dissolved in anhydrous tetrahydrofuran (10 milliliters). The mixture was stirred for about 60 minutes while warming up to room temperature, and thickened to form a gelatinous slurry. FTIR spectroscopic analysis of a reaction sample showed little unreacted isocyanate (peak at 2180 cm$^{-1}$, sample prepared as a KBr pellet). Any residual isocyanate was quenched by addition of methanol (5 milliliters). The reaction mixture was then filtered by vacuum filtration to give a semi-solid product, which was subsequently stirred in hexane to ensure full precipitation. The solid product was filtered and dried in air to give 8.17 grams of a white powder (79 percent yield). The product was believed to be of the formulae

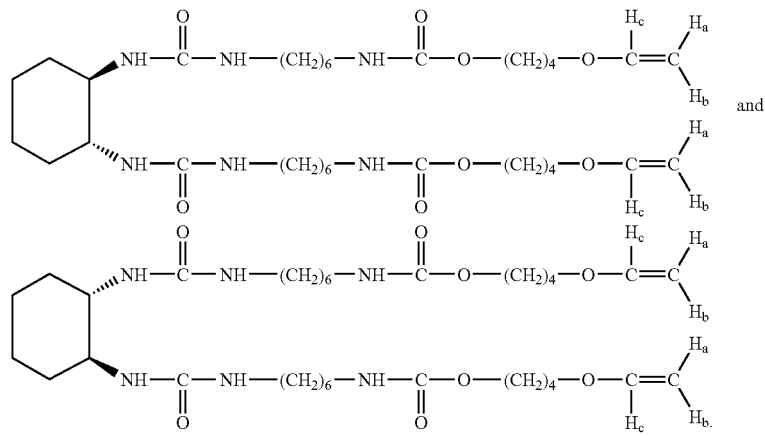

and $^1$H-NMR spectroscopic analysis of the solid was performed in DMSO-$d_6$ (300 mHz) at high temperature (60° C.) and indicated the above structure with the following assigned peaks: 1.05-1.90 ppm (several multiplets, 16 H integration, 4 methylene protons from 1,4-butanediol vinyl ether portion, 8 methylene protons from the 1,6-diisocyanatohexane portion, and 4 methylene protons from the cyclohexane ring portion); 2.95 ppm (multiplet, 4 H integration, —NH(C=O)NHCH$_2$(CH$_2$)$_4$CH$_2$NH(C=O)O—); 3.2 ppm (broad singlet, 1 H integration, tertiary methane proton adjacent to urea group on cyclohexane ring); 3.70 ppm (multiplet, 2 H integration, NH(C=O)O(CH$_2$)$_4$—O—C(H$_c$)=C(H$_a$)(H$_b$)); 3.96 ppm (doublet, 1 H integration, —O—C(H$_c$)=C(H$_a$)(H$_b$)); 3.98 ppm (multiplet, 2 H integration, NH(C=O)OCH$_2$CH$_2$CH$_2$CH$_2$—O—C(H$_c$)=C(H$_a$)(H$_b$)); 4.20 ppm (doublet, 1 H integration, —O—C(H$_c$)=C(H$_a$)(H$_b$)); 5.60 ppm and 5.72 ppm (broad singlets, each 1 H integration, urea NH protons); 6.48 ppm (doublet of doublets, 1 H integration, —O—C(H$_c$)=C(H$_a$)(H$_b$)); 6.82 ppm (broad singlet, 1 H integration, urethane NH proton). Elemental analysis calculated for C: 59.80%, H: 9.15%, N: 12.31%; found for C: 59.36%, H: 9.53%, N: 12.58%.

EXAMPLE XVIII

Into a solution containing 1,12-diisocyanatododecane (5.04 grams, 20 mmol; obtained from Sigma-Aldrich Fine Chemicals) and a 1:1 mixture of hexane and tetrahydrofuran (75 milliliters) stirring at room temperature was added a solution containing triethylene glycol monomethacrylate (4.36 grams, 20 mmol; obtained as CD570 from Sartomer Company Inc., Exton, Pa.) dissolved in a 1:1 mixture of hexane and tetrahydrofuran (25 milliliters), and dibutyltin dilaurate (0.063 grams, 0.1 mmol; obtained from Sigma-Aldrich Fine Chemicals) as the catalyst. The mixture was stirred and heated to an internal temperature of 40° C. The progress of the reaction was monitored by $^1$H-NMR spectroscopy for consumption of the triethylene glycol monomethacrylate reactant. The mixture was cooled to about 15° C. temperature, after which to this mixture was added dropwise a solution of trans-1,2-diaminocyclohexane (1.14 grams, 10 mmol; obtained as a racemic mixture of (1R,2R) and (1S,2S) stereoisomers from Sigma-Aldrich Fine Chemicals) dissolved in a 1:1 mixture of hexane and tetrahydrofuran (20 milliliters). The reaction mixture was stirred for 1 hour while warming up to room temperature. FTIR spectroscopic analysis of a reaction sample showed little unreacted isocyanate (peak at 2180 cm$^{-1}$, sample prepared as a KBr pellet). Any residual isocyanate reagent was quenched by addition of methanol (5 milliliters). The reaction mixture was then filtered by vacuum filtration to give 10.11 grams of a solid product as a white powder (96 percent yield). The product was believed to be of the formulae

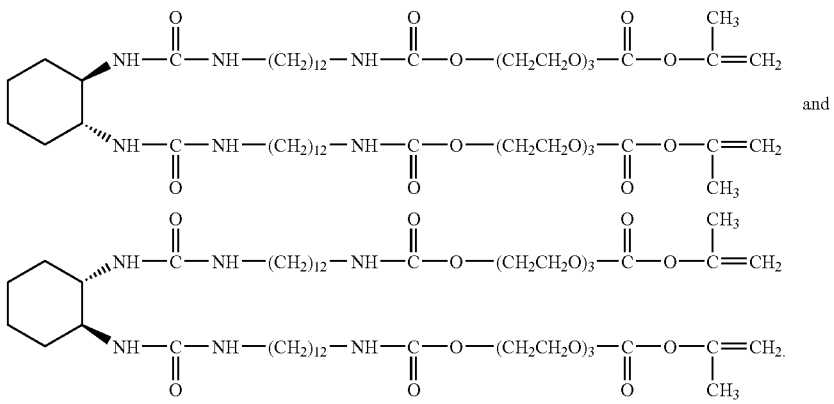

and

¹H-NMR spectroscopic analysis of the solid was performed in DMSO-d$_6$ (300 MHz) at room temperature (25° C.) and indicated the above structure with the following assigned peaks: 1.10-1.80 ppm (multiplet, 24 H integration, 20 protons from —NH—CH$_2$(CH$_2$)$_{10}$CH$_2$—NH— portion and 4 methylene protons from the cyclohexane ring portion); 1.90 ppm (singlet, 3 H integration, —(C=O)C(CH$_3$)=CH$_2$); 2.95 ppm (narrow multiplet, 4 H integration, —NH—CH$_2$(CH$_2$)$_{10}$CH$_2$—NH—); 3.35 ppm (multiplet, 1 H, cyclohexane ring methine proton); 3.55 ppm (narrow multiplet, 8 H integration, —(CH$_2$—O) protons); 4.07 ppm and 4.27 ppm (broad singlets, each 2 H integration, NH(C=O)OCH$_2$CH$_2$O— and —OCH$_2$CH$_2$O(C=O)—C(CH$_3$)=CH$_2$); 5.70 ppm and 5.88 ppm (broad singlet, each 1 H integration, urea NH protons); 5.70 ppm and 6.18 ppm (sharp singlet, each 1 H integration, terminal vinyl protons —(C=O)C(CH$_3$)=CH$_2$); 7.15 ppm (broad singlet, 1 H integration, urethane NH proton). Elemental analysis calculated for: C: 57.80%, H: 8.80%, N: 8.99%. Found for: C: 61.39%, H: 9.28%, N: 7.96%.

EXAMPLE XIX

Into a solution containing 1,6-diisocyanatohexane (4.03 grams, 24 mmol; obtained from Sigma-Aldrich Fine Chemicals) and a 1:1 mixture of hexane and tetrahydrofuran (100 milliliters) stirring at room temperature was added a solution containing triethylene glycol monomethacrylate (5.24 grams, 24 mmol; obtained as CD570 from Sartomer Company Inc., Exton, Pa.) dissolved in a 1:1 mixture of hexane and tetrahydrofuran (10 milliliters) and dibutyltin dilaurate (0.075 grams, 0.12 mmol (obtained from Sigma-Aldrich Fine Chemicals) as the catalyst. The mixture was stirred and heated to an internal temperature of 40° C. The progress of the reaction was monitored by ¹H-NMR spectroscopy for consumption of the triethylene glycol monomethacrylate reactant. The mixture was cooled to about 15° C. temperature, after which to this mixture was added dropwise a solution of trans-1,2-diaminocyclohexane (1.37 grams, 12 mmol; obtained as a racemic mixture of (1R,2R) and (1S,2S) stereoisomers from Sigma-Aldrich Fine Chemicals) dissolved in a 1:1 mixture of hexane and tetrahydrofuran (10 milliliters). The reaction mixture was stirred for 1 hour while warming up to room temperature. FTIR spectroscopic analysis of a reaction sample showed little unreacted isocyanate (peak at 2180 cm⁻¹, sample prepared as a KBr pellet). Any residual isocyanate reagent was quenched by addition of methanol (5 milliliters). The reaction mixture was then filtered by vacuum filtration to give 6.13 grams of a solid product as a white powder (58 percent yield). ¹H-NMR spectroscopic analysis of the solid was performed in DMSO-d$_6$ (300 MHz) at room temperature (25° C.) and exhibited spectral assignments that matched those found for the compound in Example XVIII. The product was believed to be of the formulae

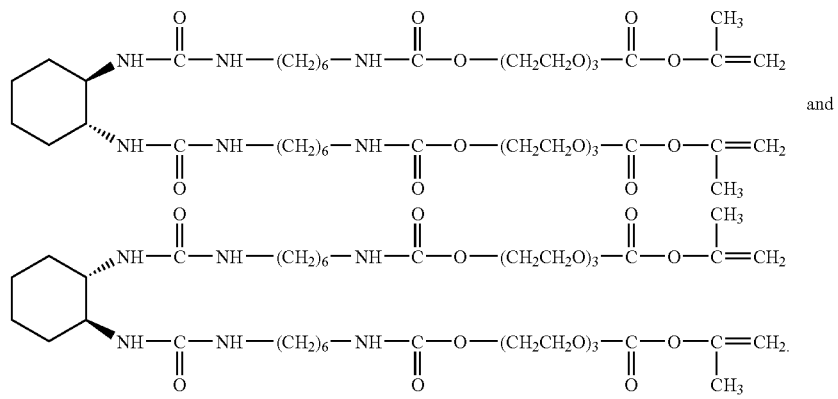

and

What is claimed is:

1. A process for preparing bis[urea-urethane] compounds of the formula

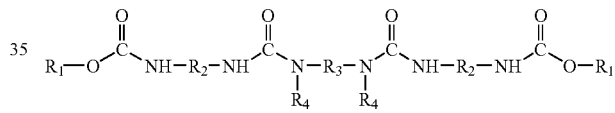

wherein R$_1$ is an alkyl group, an aryl group, an arylalkyl group, or an alkylaryl group, R$_2$ is an alkylene group, an arylene group, an arylalkylene group, or an alkylarylene group, R$_3$ is an alkylene group, an arylene group, an arylalkylene group, or an alkylarylene group, and R$_4$ is a hydrogen atom or an alkyl group, said process comprising: (1) first bring to a reaction temperature of from about 20 to about 125° C. a reaction mixture comprising a monoalcohol reactant of the formula R$_1$—OH, a diisocyanate reactant of the formula OCN—R$_2$—NCO and a Lewis acid catalyst, said monoalcohol being present in an amount of from about 0.8 to about 1.2 moles of monoalcohol per every one mole of diisocyanate, said monoalcohol and said diisocyanate reactants being admixed in a solvent, said reactants and said solvent being present in relative amounts of about 1 milliliter or more of solvent per every 1 millimole of diisocyanate, said reaction temperature continuing until reaction between the monoalcohol and the diisocyanate is complete; and (2) subsequent to step (1), adding to the reaction mixture a diamine of the formula

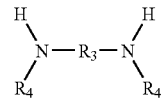

without isolating the reaction product of step (1), thereby forming a compound of the formula

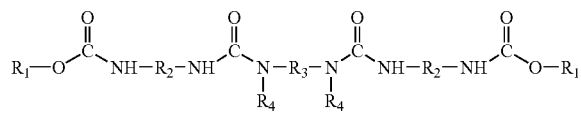

in desirably high yield and high purity.

2. A process according to claim 1 wherein the monoalcohol reactant and the diisocyanate reactant are present in an amount of no more than about 1 mole of monoalcohol per every one mole of diisocyanate.

3. A process according to claim 1 wherein said reactants and said solvent are present in a relative amount of about 3 milliliters or more of solvent per every 1 millimole of diisocyanate.

4. A process according to claim 1 wherein said reactants and said solvent are present in a relative amount of about 5 milliliters or more of solvent per every 1 millimole of diisocyanate.

5. A process according to claim 1 wherein said reactants and said solvent are present in a relative amount of about 8 milliliters or more of solvent per every 1 millimole of diisocyanate.

6. A process according to claim 1 wherein said reactants and said solvent are present in a relative amount of about 10 milliliters or more of solvent per every 1 millimole of diisocyanate.

7. A process according to claim 1 wherein said reactants and said solvent are present in a relative amount of about 20 milliliters or more of solvent per every 1 millimole of diisocyanate.

8. A process according to claim 1 wherein said reactants and said solvent are present in a relative amount of about 30 milliliters or more of solvent per every 1 millimole of diisocyanate.

9. A process according to claim 1 wherein said reaction temperature is about 40° C. or greater.

10. A process according to claim 1 wherein said reaction temperature is about 50° C. or greater.

11. A process according to claim 1 wherein the Lewis acid catalyst is selected from the group consisting of dibutyl tin dilaurate, bismuth tris-neodecanoate, cobalt benzoate, lithium acetate, stannous octoate, triethylamine, ferric chloride, aluminum trichloride, boron trichloride, boron trifluoride, titanium tetrachloride, tin tetrachloride and mixtures thereof.

12. A process according to claim 1 wherein reaction temperature is no more than about 75° C.

13. A process according to claim 1 wherein the diamine is added to the reaction mixture in an amount of from about 1.75 to about 2.3 moles of the reaction product of step (2) per every one mole of diamine.

14. A process according to claim 1 wherein the diamine is added to the reaction mixture in an amount of from about 1.9 to about 2.1 moles of the reaction product of step (1) per every one mole of diamine.

15. A process according to claim 1 wherein the diamine is added to the reaction mixture in an amount of about 2 moles of the reaction product of step (1) per every one mole of diamine.

16. A process according to claim 1 wherein the diamine and the reaction product of step (1) react at a temperature of from about 10 to about 75° C.

17. A process according to claim 1 wherein the diamine and the reaction product of step (1) react at a temperature of from about 20 to about 50° C.

18. A process according to claim 1 wherein the diamine and the reaction product of step (1) react at a temperature of from about 30 to about 40° C.

19. A process for preparing bis[urea-urethane] compounds of the formula

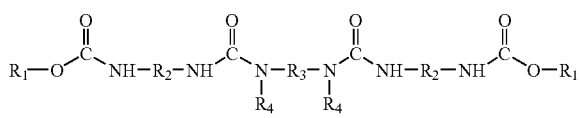

wherein $R_1$ is an alkyl group, an aryl group, an arylalkyl group, or an alkylaryl group, $R_2$ is an alkylene group, an arylene group, an arylalkylene group, or an alkylarylene group, $R_3$ is an alkylene group, an arylene group, an arylalkylene group, or an alkylarylene group, and $R_4$ is a hydrogen atom or an alkyl group, said process comprising: (1) first bring to a reaction temperature of from about 20 to about 125° C. a reaction mixture comprising a monoalcohol reactant of the formula $R_1$—OH, a diisocyanate reactant of the formula OCN—$R_2$—NCO and a Lewis acid catalyst, said monoalcohol being present in an amount of from about 0.8 to about 1.2 moles of monoalcohol per every one mole of diisocyanate, said mono alcohol and said diisocyanate reactants being admixed in a solvent, said reactants and said solvent being present in relative amounts of about 7 milliliters or more of solvent per every 1 millimole of diisocyanate, said reaction temperature continuing until reaction between the monoalcohol and the diisocyanate is complete; and (2) subsequent to step (1), adding to the reaction mixture a diamine of the formula

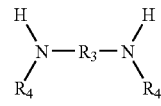

without isolating the reaction product of step (1), said addition being in an amount of from about 1.75 to about 2.3 moles of the reaction product of step (1) per every one mole of diamine, thereby forming a compound of the formula

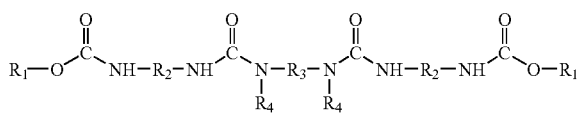

in desirably high yield and high purity.

20. A process for preparing bis[urea-urethane] compounds of the formula

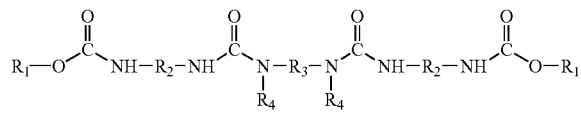

wherein $R_1$ is an alkyl group, an aryl group, an arylalkyl group, or an alkylaryl group, $R_2$ is an alkylene group, an arylene group, an arylalkylene group, or an alkylarylene group, $R_3$ is an alkylene group, an arylene group, an arylalkylene group, or an alkylarylene group, and $R_4$ is a hydrogen atom or an alkyl group, said process comprising: (1) first bring to a reaction temperature of from about 20 to about 125° C. a reaction mixture comprising a monoalcohol reactant of the formula $R_1$—OH, a diisocyanate reactant of the formula OCN—$R_2$—NCO and a Lewis acid catalyst, said monoalcohol being present in an amount of from about 0.8 to about 1 moles of monoalcohol per every one mole of diisocyanate, said monoalcohol and said diisocyanate reactants being admixed in a solvent, said reactants and said solvent being present in relative amounts of at about 7 milliliters or more of solvent per every 1 millimole of diisocyanate, said reaction temperature continuing until reaction between the monoalcohol and the diisocyanate is complete; and (2) subsequent to step (1), adding to the reaction mixture a diamine of the formula

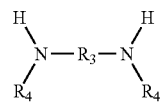

without isolating the reaction product of step (1), said addition being in an amount of from about 1.9 to about 2.1 moles of the reaction product of step (1) per every one mole of diamine, thereby forming a compound of the formula

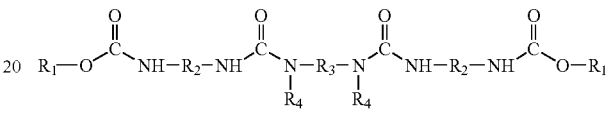

in desirably high yield and high purity.

* * * * *